US006080568A

United States Patent [19]
Day et al.

[11] Patent Number: 6,080,568
[45] Date of Patent: Jun. 27, 2000

[54] MUTANT α-AMYLASE COMPRISING MODIFICATION AT RESIDUES CORRESPONDING TO A210, H405 AND/OR T412 IN *BACILLUS LICHENIFORMIS*

[75] Inventors: Anthony G. Day; Barbara A. Swanson, both of San Francisco, Calif.

[73] Assignee: Genencor International, Inc., Rochester, N.Y.

[21] Appl. No.: 08/914,679

[22] Filed: Aug. 19, 1997

[51] Int. Cl.[7] .............................. C12N 9/28; C12N 15/00; C08B 30/04; C11D 0/00
[52] U.S. Cl. ........................ 435/202; 435/201; 435/203; 435/275; 435/832; 435/836; 435/440; 570/226; 570/235; 570/320; 570/392
[58] Field of Search ................................ 435/202, 275, 435/832, 836, 201, 203, 440; 510/226, 235, 320, 392

[56] References Cited

U.S. PATENT DOCUMENTS

| | | | |
|---|---|---|---|
| Re. 34,606 | 5/1994 | Estell et al. | 510/392 |
| 4,261,868 | 4/1981 | Hora et al. | 510/393 |
| 4,284,722 | 8/1981 | Tamuri et al. | 435/94 |
| 4,493,893 | 1/1985 | Mielenz et al. | 435/91.41 |
| 4,620,936 | 11/1986 | Kielman et al. | 510/226 |
| 4,634,551 | 1/1987 | Burns et al. | 510/313 |
| 4,732,973 | 3/1988 | Barr et al. | 530/350 |
| 4,752,585 | 6/1988 | Koths et al. | 435/252.33 |
| 4,760,025 | 7/1988 | Estell et al. | 510/392 |
| 4,863,626 | 9/1989 | Coyne et al. | 510/530 |
| 5,118,623 | 6/1992 | Boguslawski et al. | 510/530 |
| 5,322,778 | 6/1994 | Antrim et al. | 435/99 |
| 5,346,823 | 9/1994 | Estell et al. | 435/222 |
| 5,364,782 | 11/1994 | Quax et al. | 435/202 |
| 5,763,385 | 6/1998 | Bott et al. | 510/392 |

FOREIGN PATENT DOCUMENTS

| | | |
|---|---|---|
| 0946/92 | 7/1992 | Denmark . |
| 1503/92 | 12/1992 | Denmark . |
| 0 130 756 | 9/1985 | European Pat. Off. . |
| 0 208 491 | 1/1987 | European Pat. Off. . |
| 0 251 446 | 1/1988 | European Pat. Off. . |
| 0 273 268 | 7/1988 | European Pat. Off. . |
| 0 285 123 | 10/1988 | European Pat. Off. . |
| 0 378 261 | 7/1990 | European Pat. Off. . |
| 0 409 299 A2 | 1/1991 | European Pat. Off. . |
| 0 410 498 A2 | 1/1991 | European Pat. Off. . |
| 02 676 456 | 11/1992 | France . |
| WO 91/00353 | 1/1991 | WIPO . |
| WO 91/16423 | 10/1991 | WIPO . |
| WO 92/08778 | 5/1992 | WIPO . |
| WO 94/02597 | 2/1994 | WIPO . |
| WO 94/18314 | 8/1994 | WIPO . |
| WO 95/10603 | 4/1995 | WIPO . |
| WO 95/35382 | 5/1995 | WIPO . |
| WO 96/05295 | 2/1996 | WIPO . |

OTHER PUBLICATIONS

Bealin–Kelly et al., "Studies on the Thermostability of the αamylase of *Bacillus caldovelox*," Appl Microbiol Biotechnol (1991) 36:332–336.

Bierbaum et al., "Production of protease with *Bacillus licheniformis* mutants insensitive to repression of exoenzyme biosynthesis," Appl Microbiol Biotechnol (1994) 40:611–617.

Boel et al., "Calcium Binding in α–Amylases: An X–ray Diffraction Study at 2.1–ÅResolution of Two Enzymes from Aspergillus," *Biochemistry* (1990) 29:6244–6249.

Bott et al., "the Three–dimensional Structure of *Bacillus amyloliquefaciens* Subtilisin at 1.8 Å and an Analysis of the Structural Consequences of Peroxide Inactivation," *J Biol Chem* (1988) 263:7895–7906.

Brady et al., "Solution of the Structure of *Aspergillus niger* Acid α–Amylase by Combined Molecular Replacement and Multiple Isomorphous Replacement Methods," *Acta Cryst* (1991) 47:527–535.

Brayer et al., "The structure of human pancreatic α–amylase at 1.8 Å resolution and comparisons with related enzymes," *Prot Science* (1995) 4:1730–1742.

Brosnan et al. "Investigation of the mechanisms of irreversible thermoinactivation of *Bacillus stearothermophilus* α–amylase," *Eur J Biochem* (1992) 203:225–231.

Burley et al., Aromatic–Aromatic Interaction: A Mechanism of Protein Structure Stabilization,: *Science* (1985) 229:23–28.

Byrne et al., "Energetic Contribution of side Chain Hydrogen Bonding to the Stability of Staphylococcal Nuclease," *Biochemistry* (1995) 34:13949–13960.

Chang et al., "Crystallization and Preliminary X–ray Crystallographic Analysis of α–Amylase from *Bacillus subtilis*," *J Mol Biol* (1993) 229:235–238.

Chen et al., "Identification and elimination by site–directed mutagenesis of thermolabile aspartyl bonds in *Aspergillus awamore* glucoamylase," *Protein Engineering* (1995) 8:575–582.

Clarke et al., "Engineered Disulfide Bonds as Probes of the Folding Pathway of Barnase: Increasing the Stability of Proteins against the Rate of Denaturation," *Biochemistry* (1993) 32:4322–4329.

Dao–pin et al., "Contributions of Engineered Surface Salt Bridges to the Stability of T4 Lysozyme Determined by Directed Mutagenesis," *Biochemistry* (1991) 30:7142–7153.

Declerck, et al. "Use of Amber Suppressors to Investigate the Thermostability of *Bacillus licheniformis* α–Amylase," *J Biol Chem* (1990) 265:15481–15488.

Delboni et al., "Crystal structure of recombinant triosephosphate isomerase from *Bicillus stearothermophilus*. An analysis of potential thermostability factors in six isomerases with known three–dimensional structures points to the improtance of hydrophobic interactions," *Protein Science* (1995) 4:2594–2604.

(List continued on next page.)

*Primary Examiner*—Rebecca E. Prouty
*Assistant Examiner*—Elizabeth Slobodyansky
*Attorney, Agent, or Firm*—Christopher L. Stone

[57] ABSTRACT

Novel α-amylase enzymes are disclosed in which one or more of residues corresponding to A210, H405 and T412 in *Bacillus licheniformis* are mutated. The disclosed α-amylase enzymes show altered or improved stability and/or activity profiles.

11 Claims, 9 Drawing Sheets

OTHER PUBLICATIONS

Doig et al., "N– and C–capping preferences for all 20 amino acids in α–helical peptides," *Protein Science* (1995) 4:1325–1336.

Eder et al., "Folding of Subtilisin BPN': Characterization of a Folding Intermediate," *Biochemistry* (1993) 32:18–26.

Eriksson et al., "Response of a Protein Structure to Cavity––Creating Mutations and its Relation to the Hydrophobic Effect," *Science* (1992) 255:178–183.

Estell et al. "Engineering an Enzyme by Site–directed Mutagenesis to be Resistant to Chemical Oxidation," *J Biol Chem* (1985) 260:6518–6521.

Fágáin, "Understanding and increasing protein stability," *Biochimica et Biophysica Acta* (1995) 1252:1–14.

Gong et al., "Hydrolysis of Cellulose: Mechanisms of Enzymatic and Acid Catalysis," Advances in Chemistry Series, American Chemical Society, Washington, D.C. 1979, pp. 261–287.

Gray et al., "Structural Genes Encoding the Thermophilic α–amylases of *Bacillus stearothermophilus* and *Bacillus licheniformis*," *J Bacteriol* (1986) 166:635–643.

Hahn et al., "Crystal Structure and Site–directed Mutagenesis of *Bacillus macerans* Endo–1,3–1,4– β–glucanase," *J Biol Chem* (1995) 270:3081–3088.

Hakansson et al., "Purification and Characterization of a Low Molecular Weight 1,4–β–Glucan Glucanohydrolase from the Cellulolytic Fungus Trichoderma Viride QM 9414," *Biochimica et Biophysica Acta* (1978) 524:385–392.

Holm et al., "Random mutagenesis used to probe the structure and function of *Bacillus stearothermophilus* alpha–amylase," *Prot. Engineering* (1990) 3:181–191.

Janecek et al., "α–Amylases and approaches leading to their enhanced stability," *FEBS* (1992) 304:1–3.

Janecek et al., "Evolution of Parallel β/α Barrel Enzyme Family Lightened by Structural Data on Starch–Processing Enzymes," *J Prot Chem* (1993) 12:509–514.

Janecek, "Sequence similarities and evolutionary relationships of microbial, plant and animal α–amylases," *Eur J Biochem* (1994) 224:519–524.

Janecek, "Sequence similarities in $(\alpha/\beta)_8$–barrel enzymes revealed by conserved regions of α–amylase," *FEBS* (1993) 316:23–26.

Janse et al., "Regional sequence homologies in starch–degrading enzymes," *Curr Genet* (1993) 24:400–407.

Jespersen et al., "Starch– and Glycogen–Debranching and Branching Enzymes: Prediction of Structural Features of the Catalytic $(\alpha/\beta)_8$–Barrel Domain and Evolutionary Relationship to Other Amylolytic Enzymes," *J Prot Chem* (1993) 12:791–805.

Jorgensen et al., "Cloning of a chromosomal α–amylase gene from *Bacillus stearothermophilus*," *FEMS Microbiol Letters* (1991) 77:271–276.

Joyet et al. "Hyperthermostable variants of a highly thermostable alpha–amylase," *Biotech* (1992) 10:1579–1583.

Kadziola et al. "Crystal and Molecular Structure of Barley α–Amylase," *J Mol Biol* (1994) 239:104–121.

Kellis Jr. et al., "Contribution of hydrophobic interactions to protein stability," *Nature* (1988) 333:784–786.

Kidd et al., "A Weak Calcium Binding Site in Subtilisin BPN' has a Dramatic Effect on Protein Stability," *J. Am. Chem. Soc.* (1996) 118:1645–1650.

Kim et al., "Changes in Optimum pH and Thermostability of α–Amylase from *Bacillus licheniformis* by Site–directed Mutagenesis of His 235 and Asp 328," *Bull. Korean Chem. Soc.* (1994) 15:832–835.

Larson et al., "Refined Molecular Structure of Pig Pancreatic α–Amylase at 2–1 Å Resolution," *J Mol Biol* (1994) 235:1560–1584.

Lehmann et al., "Differential chemical modification of substrate binding areas in porcine–pancreatic alph–amylase by three regioisomeric photolabile ligands," *Carbohydrate Research* (1994) 265:19–30.

MacGregor et al., "Relationships between Structure and Activity in the α–Amylase Family of Starch–metabolising Enzymes," *Starch* (1993) 45:232–237.

Machius et al., "Crystal Structure of Calcium–depleted *Bacillus licheniformis* α–amylase at 2.2 Å Resolution," *J Mol Biol* (1995) 246:545–559.

Malcolm et al., "Ancestral lysozymes reconstructed, neutrality tested, and thermostability linked to hydrocarbon packing," *Nature* (1990) 345:86–89.

Manning et al., "Thermostable α–amylase of *Bacillus stearothermophilus*," *J Biol Chem* (1961) 236:2952–2965.

Matsui et al., "A mutant α–amylase with enhanced activity specific for short substrates," *FEBS* (1992) 310:216–218.

Matsui et al., "An increase in the transglycosylation activity of Saccharomycopsis α–amylase altered by site–directed mutagenesis," *Biochimica et Biophysica Acta* (1991) 1077:416–419.

Matsui et al., "Roles of the Aromatic Residues Conserved in the Active Center of Saccharomycopsis α–Amylase for Transglycosylation and Hydrolysis Activity," *Biochem* (1994) 33:451–458.

Matsuura et al., "Structure and Possible Catalytic Residues of Taka–Amylase A," *J Biochem* (1984) 95:697–702.

Matthews et al., "Solvent Content of Protein Crystals," *J Mol Biol* (1968) 33:491–497.

Matthews, "Structural and Genetic Analysis of Protein Stability," *Annu. Rev. Biochem.* (1993) 62:139–160.

Mazur et al., "The Catalytic Mechanism of α–Amylase Based Upon Enzyme Crystal Structures and Model Building Calculations," *Biochem Biophys Res Com* (1994) 204:297–302.

Mecham et al., "Trypsin–Like Neutral Protease Associated with Soluble Elastin," *Biochem* (1977) 16:3825–3831.

Mitchinson et al., "Protein Engineering of Disulfide Bonds in Subtilisin BPN'," *Biochemistry* (1989) 28:4807–4815.

Mizuno et al., "Crystallization and Preliminary X–ray Studies of Wild Type and Catalaytic–site Mutant α–Amylase from *bacillus subtilis*," *J Mol Biol* (1993) 234:1282–1283.

Mosimann et al. "A Critical Assessment of Comparative Molecular Modeling of Tertiary Structures of Proteins," *Prot* (1995) 23:301–317.

Moult et al., "A Large–Scale Experiment to Assess Protein Structure Prediction Methods," *Prot* (1995) 23:ii–iv.

Muir et al., "Citrate synthase from the hyperthermophilic Archaeon, *Pyrococcus furiosus*," *Protein Engineering* (1995) 8:583–592.

Nakajima et al., "Nucleotide Sequence of the *Bacillus stearothermophilus* α–Amylase Gene," *J Bacteriol* (1985) 163:401–406.

Nakatani et al., "Effect of Modifying histidine residues on the action of *Bacillus amyloliquefaciens* and barley–malt α–amylase," *Carbohydrate Research* (1994) 257:155–161.

Nicholson et al., "Enhanced protein thermostability from designed mutations that interact with α–helix dipoles," *Nature* (1988) 336:651–656.

Ogasahara et al., Studies on Thermophilic α–Amylase from *Bacillus stearothermophilus*, section I, *J Biochem* 67:65–75.

Ogasahara et al., Studies on Thermophilic α–Amylase from *Bacillus stearothermophilus*, section II, *J Biochem* 67:65–75.

Ottesen et al., "The Subtilisins," *Methods in Enzymology* Chapter 11 pp. 199–215.

Pantoliano et al., "The Engineering of Binding Affinity at Metal Ion Binding Sites for the Stabilization of Proteins: Subtilisin as a Test Case," *Biochemistry* (1988) 27:8311–8317.

Perry et al., "Disulfide Bond Engineered into T4 Lysozyme: Stabilization of the Protein Toward Thermal Inactivation," *Science* (1984) 226:555–557.

Qian et al., "Structure and Molecular Model Refinement of Pig Pancreatic α–Amylase at 2–1 Å Resolution," *J Mol Biol* (1993) 231:785–799.

Qian et al., "The Active Center of a Mammalian α–Amylase. Structure of the Complex of a Pancreatic α–Amylase with a Carbohydrate Inhibitor Refined to 2.2 Å Resolution," *Biochem* (1994) 33:6284–6294.

Ramasubbu et al., "Crystallization and Preliminary X–Ray Diffraction Studies of Human Salivary α–amylase," *Prot* (1991) 11:230–232.

Richardson et al., "Amino Acid Preferences for Specific Locations at the Ends of α Helices," *Science* (1988) 240:1648–1652.

Russell et al., "Engineering thermostability: lessons from thermophilic proteins," *Current Opinion in Biotechnology* (1995) 6:370–374.

Samudrala et al., "Confronting the Problem of Interconnected Structural Changes in the Comparative Modeling of Proteins," *Prot* (1995) 23:327–336.

Shih et al., "Design and structural analysis of an engineered thermostable chicken lysozyme," *Protein Science* (1995) 4:2063–2072.

Siezen et al., "Homology modelling and protein engineering strategy of subtilases, the family of subtilisin–like serine proteinases," (1991) 719–737.

Sogaard et al., "α–Amylases: Structure and function," *Carbohydrate Polymers* (1993) 21:137–146.

Sogaard et al., "Site–directed Mutagenesis of Histidine 93, Aspartic Acid 180, Glutamic Acid 205, Histidine 290, and Aspartic Acid 291 at the Active Site and Tryptophan 279 at the Raw Starch Binding Site in Barley α–amylase 1," *J Biol Chem* (1993) 268:22480–22484.

Staberg, "Cellulases—The enzymes," Ph.D. Thesis—Uppsala University pp. 16–18.

Strausberg et al., "Directed Evolution of a Subtilisin with Calcium–Independent Stability," *Bio/Technology* (1995) 13:669–672.

Strokopytov et al., "X–ray Structure of Cyclodextrin Glycosyltransferase Complexed with Acarbose. Implications for the Catalytic Mechanism of Glycosidases," *Biochem* (1995) 34:2234–2240.

Suzuki et al. "Crystallization and Preliminary Crystallographic Study of Bacterial α–Amylases," *J Biochem* (1990) 108:379–381.

Suzuki et al., "Amino Acid Residues Stabilizing a Bacillus α–Amylase against Irreversible Thermoinactivation," *J Biol Chem* (1989) 264:18933–18938.

Svendsen, "Chemical Modifications of the Subtilisins with Special Reference to the Binding of Large Substrates. A Review." *Review: Carlsberg Res. Commun* (1976) 41:237–291.

Svensson et al., "Mutational analysis of glycosylase function," *J Biotech* (1993) 29:1–37.

Svensson, "Protein engineering in the α–amylase family: catalytic mechanism, substrate specificity, and stability," *Plant Mol Biol* (1994) 25:141–157.

Swift et al., "Structure and Molecular Model Refinement of *Aspergillus oryzae* (TAKA) α–Amylase: an Application of the Simulated–Annealing Method," *Acta Cryst* (1991) 47:544–548.

Szilágyi et al., "Structural basis for the extreme thermostability of D–glyceraldehyde–3–phosphate dehydrogenase form *Thermotoga maritima*: analysis based on homology modelling," *Protein Engineering* (1995) 8:779–789.

Takase et al., "Site–directed mutagenesis of active site residues in *Bacillus subtilis* α–amylase," *Biochemica et Biophysica Acta* (1992) 1120:281–288.

Tanner et al., "Determinants of Enzyme Thermostability Observed in the Molecular Structure of *Thermus acquaticus* D–Glyceraldehyde–3–phosphate Dehydrogenase at 2.5 Å Resolution," *Biochemistry* (1996) 35:2597–2609.

Tomazic et al., "Why is One Bacillus α–Amylase More Resistant against Irreversible Thermoinactivation than Another?" *J Biol Chem* (1988) 263:3092–3096.

Tomazic et al., "Mechanisms of Irreversible Thermal Inactivation of Bacillus α–Amylases" *J. of Biol. Chem.* 292(7):3086–3091 (Mar. 1988).

Ulker et al., "Production and characterization of an unglycosilated low molecular weight 1, 4–β–glucan–glucanohydrolase of *Trichoderma reesei,*" *Trichoderma reesei* cellulases, Ch. 5 pp.60–77.

Vallee et al., "Characterization, Crystallization and Preliminary X–ray Crystallographic Analysis of the Complex between Barley α–Amylase and the Bifunctional α–Amylase/Subtilisin Inhibitor from Barley Seeds," *J Mol Biol* (1994) 236:368–371.

Vallee et al., "Metal Content of α–Amylases of Various Origins," *Journal of Biological Chemistry* (1959) 234:2901–2905.

Vihinen et al., "C–terminal truncations of a thermostable *Bacillus stearothermophilus* α–amylase," *Prot Engineering* (1994) 7:1255–1259.

Vihinen et al., "Site–Directed Mutagenesis of a Thermostable α–Amylase from *Bacillus stearothermophilus*: Putative Role of Three Conserved Residues," *J Biochem* (1990) 107:267–272.

von der Osten et al., "Protein engineering of subtilisins to improve stability in detergent formulations," *J Biochem* (1993) 28:55–68.

Walter et al., "Destabilization of a Protein Helix by Electrostatic Interactions," *J. Mol. Biol.* (1995) 252:133–143.

Warren et al., "Composition analysis of α–helices in thermophilic organisms," *Protein Engineering* (1995) 8:905–913.

Watanabe et al., "Multiple proline substitutions cumulatively thermostabilize *Bacillus cereus* ATCC7064 oligo–1, 6–glucosidase," *Eur. J. Biochem.* (1994) 226:277–283.

Wells et al., "In Vivo Formation and Stability of Engineered Disulfide Bonds in Subtilisin," *The Journal of Biological Chemistry* (1986) 261:6564–6570.

Yeong Lee et al., "Crystallization and a Preliminary X–Ray Crystallographic Study of α–Amylase from *Bacillus licheniformis*," *Arch Biochem Biophys* (1991) 291:255–257.

Zhu et al., "Phospholipase A$_2$ Engineering. The Roles of Disulfide Bonds in Structure, Conformational Stability, and Catalytic Function," *Biochemistry* (1995) 34:15307–15314.

Zuber, "Temperature adaptation of lactate dehydrogenase Structural, functional and genetic aspects," *Biophysical Chemistry* (1988) 29:171–1793.

```
                10                            30                          50
AGCTTGAAGAAGTGAAGAAGCAGAGAGGCTATTGAATAAATGAGTAGAAAGCGCCATATC 70                            90                         110
GGCGCTTTTCTTTTGGAAGAAAATATAGGGAAAATGGTACTTGTTAAAAATTCGGAATAT 130                           150                         170
TTATACAACATCATATGTTTCACATTGAAAGGGGAGGAGAATCATGAAACAACAAAAACG
                                                   M   K   Q   Q   K   R 190                           210                         230
GCTTTACGCCCGATTGCTGACGCTGTTATTTGCGCTCATCTTCTTGCTGCCTCATTCTGC
 L   Y   A   R   L   L   T   L   L   F   A   L   I   F   L   L   P   H   S   A 250                           270                         290
AGCAGCGGCGGCAAATCTTAATGGGACGCTGATGCAGTATTTTGAATGGTACATGCCCAA
 A   A   A   A   N   L   N   G   T   L   M   Q   Y   F   E   W   Y   M   P   N 310                           330                         350
TGACGGCCAACATTGGAAGCGTTTGCAAAACGACTCGGCATATTTGGCTGAACACGGTAT
 D   G   Q   H   W   K   R   L   Q   N   D   S   A   Y   L   A   E   H   G   I 370                           390                         410
TACTGCCGTCTGGATTCCCCCGGCATATAAGGGAACGAGCCAAGCGGATGTGGGCTACGG
 T   A   V   W   I   P   P   A   Y   K   G   T   S   Q   A   D   V   G   Y   G 430                           450                         470
TGCTTACGACCTTTATGATTTAGGGGAGTTTCATCAAAAAGGGACGGTTCGGACAAAGTA
 A   Y   D   L   Y   D   L   G   E   F   H   Q   K   G   T   V   R   T   K   Y 490                           510                         530
CGGCACAAAAGGAGAGCTGCAATCTGCGATCAAAAGTCTTCATTCCCGCGACATTAACGT
 G   T   K   G   E   L   Q   S   A   I   K   S   L   H   S   R   D   I   N   V 550                           570                         590
TTACGGGGATGTGGTCATCAACCACAAAGGCGGCGCTGATGCGACCGAAGATGTAACCGC
 Y   G   D   V   V   I   N   H   K   G   G   A   D   A   T   E   D   V   T   A 610                           630                         650
GGTTGAAGTCGATCCCGCTGACCGCAACCGCGTAATTTCAGGAGAACACCTAATTAAAGC
 V   E   V   D   P   A   D   R   N   R   V   I   S   G   E   H   L   I   K   A 670                           690                         710
CTGGACACATTTTCATTTTCCGGGGCGCGGCAGCACATACAGCGATTTTAAATGGCATTG
 W   T   H   F   H   F   P   G   R   G   S   T   Y   S   D   F   K   W   H   W 730                           750                         770
GTACCATTTTGACGGAACCGATTGGGACGAGTCCCGAAAGCTGAACCGCATCTATAAGTT
 Y   H   F   D   G   T   D   W   D   E   S   R   K   L   N   R   I   Y   K   F 790                           810                         830
TCAAGGAAAGGCTTGGGATTGGGAAGTTTCCAATGAAAACGGCAACTATGATTATTTGAT
 Q   G   K   A   W   D   W   E   V   S   N   E   N   G   N   Y   D   Y   L   M
```

FIG._1A

```
                 850                       870                       890
GTATGCCGACATCGATTATGACCATCCTGATGTCGCAGCAGAAATTAAGAGATGGGGCAC
 Y   A   D   I   D   Y   D   H   P   D   V   A   A   E   I   K   R   W   G   T
                 910                       930                       950
TTGGTATGCCAATGAACTGCAATTGGACGGTTTCCGTCTTGATGCTGTCAAACACATTAA
 W   Y   A   N   E   L   Q   L   D   G   F   R   L   D   A   V   K   H   I   K
                 970                       990                      1010
ATTTTCTTTTTTGCGGGATTGGGTTAATCATGTCAGGGAAAAAACGGGGAAGGAAATGTT
 F   S   F   L   R   D   W   V   N   H   V   R   E   K   T   G   K   E   M   F
                1030                      1050                      1070
TACGGTAGCTGAATATTGGCAGAATGACTTGGGCGCGCTGGAAAACTATTTGAACAAAAC
 T   V   A   E   Y   W   Q   N   D   L   G   A   L   E   N   Y   L   N   K   T
                1090                      1110                      1130
AAATTTTAATCATTCAGTGTTTGACGTGCCGCTTCATTATCAGTTCCATGCTGCATCGAC
 N   F   N   H   S   V   F   D   V   P   L   H   Y   Q   F   H   A   A   S   T
                1150                      1170                      1190
ACAGGGAGGCGGCTATGATATGAGGAAATTGCTGAACGGTACGGTCGTTTCCAAGCATCC
 Q   G   G   G   Y   D   M   R   K   L   L   N   G   T   V   V   S   K   H   P
                1210                      1230                      1250
GTTGAAATCGGTTACATTTGTCGATAACCATGATACACAGCCGGGGCAATCGCTTGAGTC
 L   K   S   V   T   F   V   D   N   H   D   T   Q   P   G   Q   S   L   E   S
                1270                      1290                      1310
GACTGTCCAAACATGGTTTAAGCCGCTTGCTTACGCTTTTATTCTCACAAGGGAATCTGG
 T   V   Q   T   W   F   K   P   L   A   Y   A   F   I   L   T   R   E   S   G
                1330                      1350                      1370
ATACCCTCAGGTTTTCTACGGGGATATGTACGGGACGAAAGGAGACTCCCAGCGCGAAAT
 Y   P   Q   V   F   Y   G   D   M   Y   G   T   K   G   D   S   Q   R   E   I
                1390                      1410                      1430
TCCTGCCTTGAAAACACAAAATTGAACCGATCTTAAAAGCGAGAAAACAGTATGCGTACGG
 P   A   L   K   H   K   I   E   P   I   L   K   A   R   K   Q   Y   A   Y   G
                1450                      1470                      1490
AGCACAGCATGATTATTTCGACCACCATGACATTGTCGGCTGGACAAGGGAAGGCGACAG
 A   Q   H   D   Y   F   D   H   H   D   I   V   G   W   T   R   E   G   D   S
                1510                      1530                      1550
CTCGGTTGCAAATTCAGGTTTGGCGGCATTAATAACAGACGGACCCGGTGGGGCAAAGCG
 S   V   A   N   S   G   L   A   A   L   I   T   D   G   P   G   G   A   K   R
                1570                      1590                      1610
AATGTATGTCGGCCGGCAAAACGCCGGTGAGACATGGCATGACATTACCGGAAACCGTTC
 M   Y   V   G   R   Q   N   A   G   E   T   W   H   D   I   T   G   N   R   S
                1630                      1650                      1670
GGAGCCGGTTGTCATCAATTCGGAAGGCTGGGGAGAGTTTCACGTAAACGGCGGGTCGGT
 E   P   V   V   I   N   S   E   G   W   G   E   F   H   V   N   G   G   S   V
```

FIG._1B

```
      1690                1710                1730
TTCAATTTATGTTCAAAGATAGAAGAGCAGAGAGGACGGATTTCCTGAAGGAAATCCGTT
  S   I   Y   V   Q   R   *

1750                1770                1790
TTTTTATTTTGCCCGTCTTATAAATTTCTTTGATTACATTTTATAATTAATTTTAACAAA 1810                1830                1850
GTGTCATCAGCCCTCAGGAAGGACTTGCTGACAGTTTGAATCGCATAGGTAAGGCGGGGA 1870                1890                1910
TGAAATGGCAACGTTATCTGATGTAGCAAAGAAAGCAAATGTGTCGAAAATGACGGTATC 1930                1950
GCGGGTGATCAATCATCCTGAGACTGTGACGGATGAATTGAAAAAGCT
```

FIG._1C

```
                    10                      30                      50
ANLNGTLMQYFEWYMPNDGQHWKRLQNDSAYLAEHGITAVWIPPAYKGTSQADVGYGAYD 70                      90                     110
LYDLGEFHQKGTVRTKYGTKGELQSAIKSLHSRDINVYGDVVINHKGGADATEDVTAVEV 130                     150                     170
DPADRNRVISGEHLIKAWTHFHFPGRGSTYSDFKWHWYHFDGTDWDESRKLNRIYKFQGK 190                     210                     230
AWDWEVSNENGNYDYLMYADIDYDHPDVAAEIKRWGTWYANELQLDGFRLDAVKHIKFSF 250                     270                     290
LRDWVNHVREKTGKEMFTVAEYWQNDLGALENYLNKTNFHSVFDVPLHYQFHAASTQGG 310                     330                     350
GYDMRKLLNGTVVSKHPLKSVTFVDNHDTQPGQSLESTVQTWFKPLAYAFILTRESGYPQ 370                     390                     410
VFYGDMYGTKGDSQREIPALKHKIEPILKARKQYAYGAQHDYFDHHDIVGWTREGDSSVA 430                     450                     470
NSGLAALITDGPGGAKRMYVGRQNAGETWHDITGNRSEPVVINSEGWGEFHVNGGSVSIY

VQR
```

FIG._2

Am-Lich = B.Licheniformis    Am-Amylo = B.amyloliquefaciens    Am-Stearo = B.stearothermophilus

```
                1                                                                          19
Am-Lich      .........MKQQ  KRLYARLLTL  LFALIFLLPH  ..........  ..........SAAA  AANLNGTLMQ  YFEWYMPNDG   60
Am-Amylo     MRGRGNMIQK     RKRTVSFRLV  LMCTLLFVSL  ..........  ..........PITK  TSAVNGTLMQ  YFEWYTPNDG
Am-Stearo    .........VLTF  HRIIRKGWMF  LLAFLLTASL  FCPTGRHAKA  AAPFNGTMMQ              YFEWYLPDDG 61                                                                         79
Am-Lich      QHWKRLQNDS  AYLAEHGITA  VWIPPAYKGT  SQADVGYGAY  DLYDLGEFHQ  KGTVRTKYGT                     120
Am-Amylo     QHWKRLQNDA  EHLSDIGITA  VWIPPAYKGL  SQSDNGYGPY  DLYDLGEFQQ  KGTVRTKYGT
Am-Stearo    TLWTKVANEA  NNLSSLGITA  LSLPPAYKGT  SRSDVGYGVY  DLYDLGEFNQ  KGTVRTKYGT 121                                                                        139
Am-Lich      KGELQSAIKS  LHSRDINVYG  DVVINHKGGA  DATEDVTAVE  VDPADRNRVI  SGEHLIKAWT                     180
Am-Amylo     KSELQDAIGS  LHSRNVQVYG  DVVLNHKAGA  DATEDVTAVE  VNPANRNQET  SEEYQIKAWT
Am-Stearo    KAQYLQAIQA  AHAAGMQVYA  DVVFDHKGGA  DGTEWWDAVE  VNPSDRNQEI  SGTYQIQAWT 181                                                                        197
Am-Lich      HFHFPGRGST  YSDFKWHWYH  FDGTDWDESR  KLNRIYKF...  ..........  QGKAWDWEVS  NENGNYDYLM       240
Am-Amylo     DFRFPGRGNT  YSDFFKWHWYH FDGADWDESR  KISRIFKFRG              EGKAWDWEVS  SENGNYDYLM
Am-Stearo    KFDFPGRGNT  YSSFKWRWYH  FDGVDWDESR  KLSRIYKFRG              IGKAWDWEVD  TENGNYDYLM 241                                                                        257
Am-Lich      YADIDYDHPD  VAAEIKRWGT  WYANELQLDG  FRLDAVKHIK  FSFLRDWVNH  VREKTGKEMF                    300
Am-Amylo     YADVDYDHPD  VVAETKKWGI  WYANELSLDG  FRIDAAKHIK  FSFLRDWVQA  VRQATGKEMF
Am-Stearo    YADLDMDHPE  VVTELKNWGK  WYVNTTNIDG  FRLDGLKHIK  FSFFPDWLSY  VRSQTGKPLF 301                                                                        317
Am-Lich      TVAEYWQNDL  GALENYLNKT  NFNHSVFDVP  LHYQFHAAST  QGGGYDMRKL  LNGTVVSKHP                    360
Am-Amylo     TVAEYWQNNA  GKLENYLNKT  SFNQSVFDVP  LHFNLQAASS  QGGGYDMRRL  LDGTVVSRHP
Am-Stearo    TVGEYWSYDI  NKLHNYITKT  NGTMSLFDAP  LHNKFYTASK  SGGAFDMRTL  MTNTLMKDQP
```

FIG._3A

```
            361                                                                               377
                                                                                              420
Am-Lich     LKSVTFVDNH  DTQPGQSLES  TVQTWFKPLA  YAFILTRESG  YPQVFYGDMY  GTKGDSQREI
Am-Amylo    EKAVTFVENH  DTQPGQSLES  TVQTWFKPLA  YAFILTRESG  YPQVFYGDMY  GTKGTSPKEI
Am-Stearo   TLAVTFVDNH  DTNPAKR..CS  HGRPWFKPLA  YAFILTRQEG  YPCVFYGDYY  GI........PQYNI 421                                                                               437
                                                                                              480
Am-Lich     PALKHKIEPI  LKARKQYAYG  AQHDYFDHHD  IVGWTREGDS  SVANSGLAAL  ITDGPGGAKR
Am-Amylo    PSLKDNIEPI  LKARKEYAYG  PQHDYIDHPD  VIGWTREGDS  SAAKSGLAAL  ITDGPGGGSKR
Am-Stearo   PSLKSKIDPL  LIARRDYAYG  TQHDYLDHSD  IIGWTREGVT  EKPGSGLAAL  ITDGAGRSKW 481                                              483                              540
Am-Lich     MYVGRQNAGE  TWHDITGNRS  EPVVINSEGW  GEFHVNGGSV  SIYVQR....  ..........
Am-Amylo    MYAGLKNAGE  TWYDITGNRS  DTVKIGSDGW  GEFHVNDGSV  SIYVQK....  ..........
Am-Stearo   MYVGKQHAGK  VFYDLTGNRS  DTVTINSDGW  GEFKVNGGSV  SVWVPRKTTV  STIARPITTR 541                    559
Am-Lich     ..........  .........
Am-Amylo    ..........  .........
Am-Stearo   PWTGEFVRWH  EPRLVAWP*
```

*FIG. 3B*

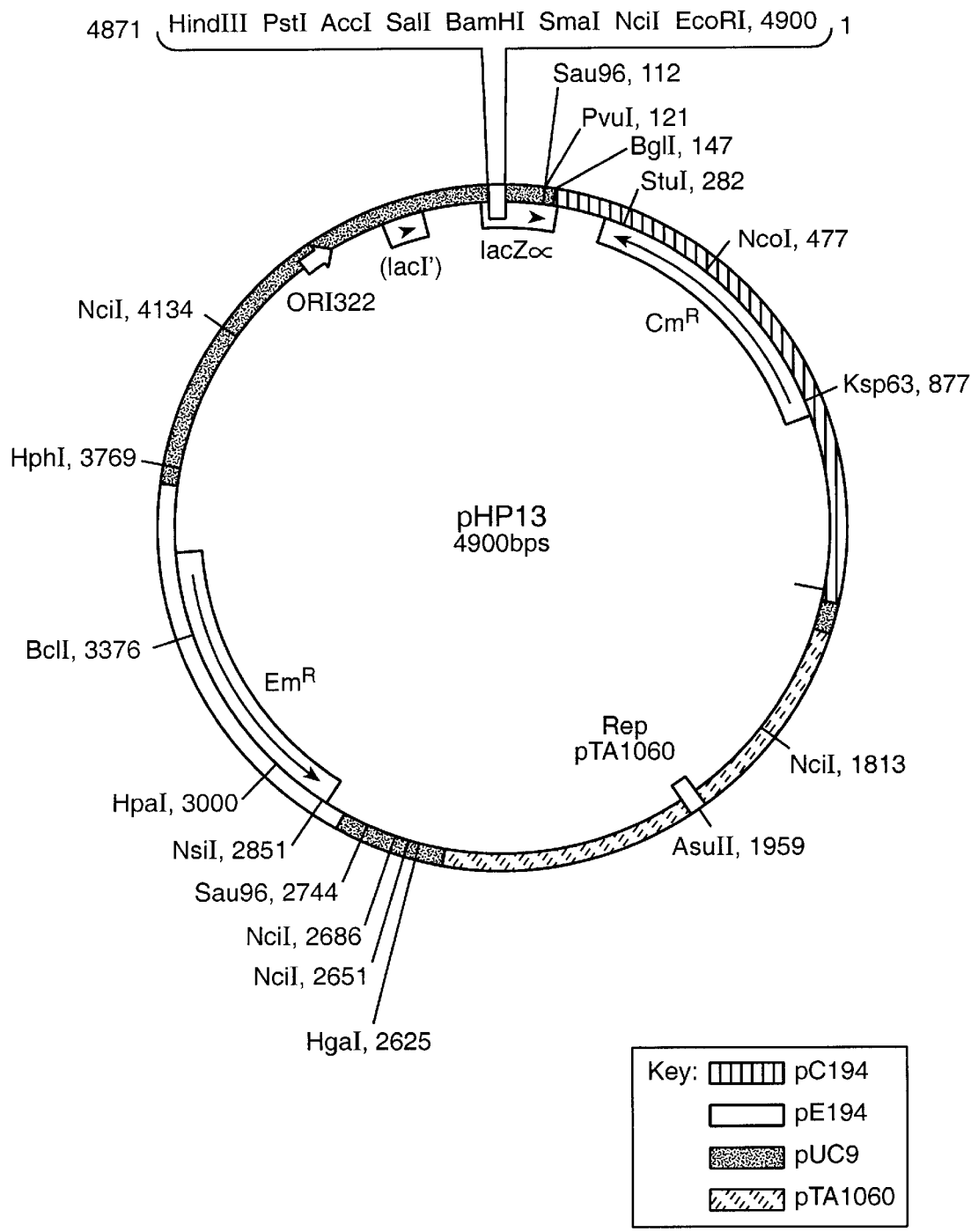
FIG._4

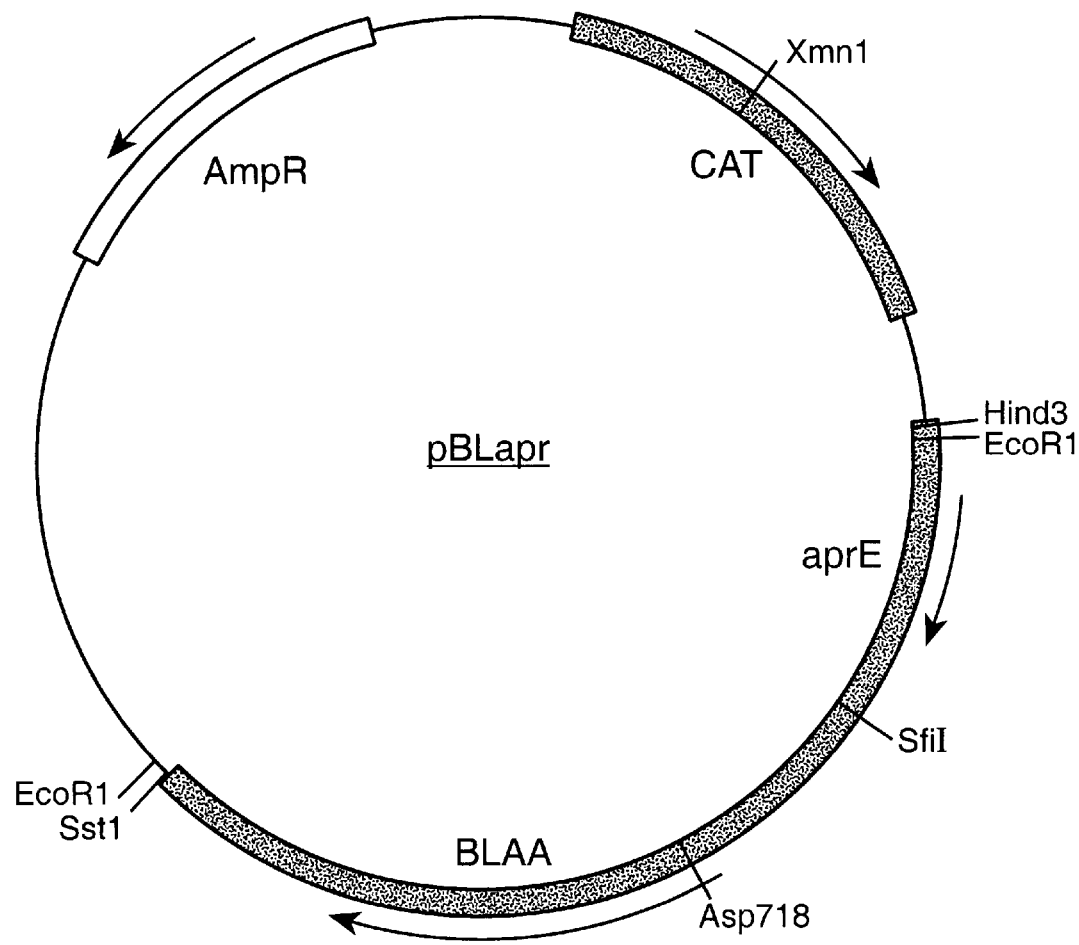
FIG._5 pHP.BL = pHP13 WITH 2460bp HindIII-EcoRI INSERT FROM pBLapr

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
      (A) LENGTH: 1968 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO: 1:

```
AGCTTGAAGA AGTGAAGAAG CAGAGAGGCT ATTGAATAAA TGAGTAGAAA GCGCCATATC      60

GGCGCTTTTC TTTTGGAAGA AAATATAGGG AAAATGGTAC TTGTTAAAAA TTCGGAATAT     120

TTATACAACA TCATATGTTT CACATTGAAA GGGGAGGAGA ATCATGAAAC AACAAAAACG     180

GCTTTACGCC CGATTGCTGA CGCTGTTATT TGCGCTCATC TTCTTGCTGC CTCATTCTGC     240

AGCAGCGGCG GCAAATCTTA ATGGGACGCT GATGCAGTAT TTTGAATGGT ACATGCCCAA     300

TGACGGCCAA CATTGGAAGC GTTTGCAAAA CGACTCGGCA TATTTGGCTG AACACGGTAT     360

TACTGCCGTC TGGATTCCCC CGGCATATAA GGGAACGAGC CAAGCGGATG TGGGCTACGG     420

TGCTTACGAC CTTTATGATT TAGGGGAGTT TCATCAAAAA GGGACGGTTC GGACAAAGTA     480

CGGCACAAAA GGAGAGCTGC AATCTGCGAT CAAAAGTCTT CATTCCCGCG ACATTAACGT     540

TTACGGGGAT GTGGTCATCA ACCACAAAGG CGGCGCTGAT GCGACCGAAG ATGTAACCGC     600

GGTTGAAGTC GATCCCGCTG ACCGCAACCG CGTAATTTCA GGAGAACACC TAATTAAAGC     660

CTGGACACAT TTTCATTTTC CGGGGCGCGG CAGCACATAC AGCGATTTTA AATGGCATTG     720

GTACCATTTT GACGGAACCG ATTGGGACGA GTCCCGAAAG CTGAACCGCA TCTATAAGTT     780

TCAAGGAAAG GCTTGGGATT GGGAAGTTTC CAATGAAAAC GGCAACTATG ATTATTTGAT     840

GTATGCCGAC ATCGATTATG ACCATCCTGA TGTCGCAGCA GAAATTAAGA GATGGGGCAC     900

TTGGTATGCC AATGAACTGC AATTGGACGG TTTCCGTCTT GATGCTGTCA AACACATTAA     960

ATTTTCTTTT TTGCGGGATT GGGTTAATCA TGTCAGGGAA AAAACGGGGA AGGAAATGTT    1020

TACGGTAGCT GAATATTGGC AGAATGACTT GGGCGCGCTG GAAAACTATT TGAACAAAAC    1080

AAATTTTAAT CATTCAGTGT TTGACGTGCC GCTTCATTAT CAGTTCCATG CTGCATCGAC    1140
```

-continued

```
ACAGGGAGGC GGCTATGATA TGAGGAAATT GCTGAACGGT ACGGTCGTTT CCAAGCATCC    1200

GTTGAAATCG GTTACATTTG TCGATAACCA TGATACACAG CCGGGGCAAT CGCTTGAGTC    1260

GACTGTCCAA ACATGGTTTA AGCCGCTTGC TTACGCTTTT ATTCTCACAA GGGAATCTGG    1320

ATACCCTCAG GTTTTCTACG GGATATGTA CGGGACGAAA GGAGACTCCC AGCGCGAAAT    1380

TCCTGCCTTG AAACACAAAA TTGAACCGAT CTTAAAAGCG AGAAAACAGT ATGCGTACGG    1440

AGCACAGCAT GATTATTTCG ACCACCATGA CATTGTCGGC TGGACAAGGG AAGGCGACAG    1500

CTCGGTTGCA AATTCAGGTT TGGCGGCATT AATAACAGAC GGACCCGGTG GGGCAAAGCG    1560

AATGTATGTC GGCCGGCAAA ACGCCGGTGA GACATGGCAT GACATTACCG GAAACCGTTC    1620

GGAGCCGGTT GTCATCAATT CGGAAGGCTG GGGAGAGTTT CACGTAAACG GCGGGTCGGT    1680

TTCAATTTAT GTTCAAAGAT AGAAGAGCAG AGAGGACGGA TTTCCTGAAG GAAATCCGTT    1740

TTTTTATTTT GCCCGTCTTA TAAATTTCTT TGATTACATT TTATAATTAA TTTTAACAAA    1800

GTGTCATCAG CCCTCAGGAA GGACTTGCTG ACAGTTTGAA TCGCATAGGT AAGGCGGGGA    1860

TGAAATGGCA ACGTTATCTG ATGTAGCAAA GAAAGCAAAT GTGTCGAAAA TGACGGTATC    1920

GCGGGTGATC AATCATCCTG AGACTGTGAC GGATGAATTG AAAAAGCT              1968
```

(2) INFORMATION FOR SEQ ID NO:2:

(i) SEQUENCE CHARACTERISTICS:
        (A) LENGTH: 511 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ala Ala Ala Asn Leu
            20                  25                  30

Asn Gly Thr Leu Met Gln Tyr Phe Glu Trp Tyr Met Pro Asn Asp Gly
        35                  40                  45

His Trp Lys Arg Leu Gln Asn Asp Ser Ala Tyr Leu Ala Glu His Gly
    50                  55                  60

Ile Thr Ala Val Trp Ile Pro Pro Ala Tyr Lys Gly Thr Ser Gln Ala
65                  70                  75                  80

Asp Val Gly Tyr Gly Ala Tyr Asp Leu Tyr Asp Leu Gly Glu Phe His
                85                  90                  95

Gln Lys Gly Thr Val Arg Thr Lys Tyr Gly Thr Lys Gly Glu Leu Gln
            100                 105                 110

Ser Ala Ile Lys Ser Leu His Ser Arg Asp Ile Asn Val Tyr Gly Asp
        115                 120                 125

Val Val Ile Asn His Lys Gly Gly Ala Asp Ala Thr Glu Asp Val Thr
    130                 135                 140

Ala Val Glu Val Asp Pro Ala Asp Arg Asn Arg Val Ile Ser Gly Glu
145                 150                 155                 160

His Leu Ile Lys Ala Trp Thr His Phe His Phe Pro Gly Arg Gly Ser
                165                 170                 175

Thr Tyr Ser Asp Phe Lys Trp His Trp Tyr His Phe Asp Gly Thr Asp
            180                 185                 190

Trp Asp Glu Ser Arg Lys Leu Asn Arg Ile Tyr Lys Phe Gln Gly Lys
```

-continued

```
                195                 200                 205
Ala Trp Asp Trp Glu Val Ser Asn Glu Asn Gly Asn Tyr Asp Tyr Leu
    210                 215                 220

Met Tyr Ala Asp Ile Asp Tyr Asp His Pro Asp Val Ala Ala Glu Ile
225                 230                 235                 240

Lys Arg Trp Gly Thr Trp Tyr Ala Asn Glu Leu Gln Leu Asp Gly Phe
                245                 250                 255

Arg Leu Asp Ala Val Lys His Ile Lys Phe Ser Phe Leu Arg Asp Trp
            260                 265                 270

Val Asn His Val Arg Glu Lys Thr Gly Lys Glu Met Phe Thr Val Ala
            275                 280                 285

Glu Tyr Trp Gln Asn Asp Leu Gly Ala Leu Glu Asn Tyr Leu Asn Lys
            290                 295                 300

Thr Asn Phe Asn His Ser Val Phe Asp Val Pro Leu His Tyr Gln Phe
305                 310                 315                 320

His Ala Ala Ser Thr Gln Gly Gly Tyr Asp Met Arg Lys Leu Leu
                325                 330                 335

Asn Gly Thr Val Val Ser Lys His Pro Leu Lys Ser Val Thr Phe Val
                340                 345                 350

Asp Asn His Asp Thr Gln Pro Gly Gln Ser Leu Glu Ser Thr Val Gln
            355                 360                 365

Thr Trp Phe Lys Pro Leu Ala Tyr Ala Phe Ile Leu Thr Arg Glu Ser
370                 375                 380

Gly Tyr Pro Gln Val Phe Tyr Gly Asp Met Tyr Gly Thr Lys Gly Asp
385                 390                 395                 400

Ser Gln Arg Glu Ile Pro Ala Leu Lys His Lys Ile Glu Pro Ile Leu
                405                 410                 415

Lys Ala Arg Lys Gln Tyr Ala Tyr Gly Ala Gln His Asp Tyr Phe Asp
            420                 425                 430

His His Asp Ile Val Gly Trp Thr Arg Glu Gly Asp Ser Ser Val Ala
            435                 440                 445

Asn Ser Gly Leu Ala Ala Leu Ile Thr Asp Gly Pro Gly Gly Ala Lys
    450                 455                 460

Arg Met Tyr Val Gly Arg Gln Asn Ala Gly Glu Thr Trp His Asp Ile
465                 470                 475                 480

Thr Gly Asn Arg Ser Glu Pro Val Val Ile Asn Ser Glu Gly Trp Gly
                485                 490                 495

Glu Phe His Val Asn Gly Gly Ser Val Ser Ile Tyr Val Gln Arg
            500                 505                 510
```

(2) INFORMATION FOR SEQ ID NO: 3:

(i) SEQUENCE CHARACTERISTICS:
        (A) LENGTH: 483 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 3:

```
Ala Asn Leu Asn Gly Thr Leu Met Gln Tyr Phe Glu Trp Tyr Met Pro
1               5                   10                  15

Asn Asp Gly Gln His Trp Lys Arg Leu Gln Asn Asp Ser Ala Tyr Leu
            20                  25                  30

Ala Glu His Gly Ile Thr Ala Val Trp Ile Pro Pro Ala Tyr Lys Gly
```

```
            35                  40                  45
Thr Ser Gln Ala Asp Val Gly Tyr Gly Ala Tyr Asp Leu Tyr Asp Leu
     50                  55                  60

Gly Glu Phe His Gln Lys Gly Thr Val Arg Thr Lys Tyr Gly Thr Lys
65                   70                  75                  80

Gly Glu Leu Gln Ser Ala Ile Lys Ser Leu His Ser Arg Asp Ile Asn
                 85                  90                  95

Val Tyr Gly Asp Val Val Ile Asn His Lys Gly Ala Asp Ala Thr
                100                 105                 110

Glu Asp Val Thr Ala Val Glu Val Asp Pro Ala Asp Arg Asn Arg Val
                115                 120                 125

Ile Ser Gly Glu His Leu Ile Lys Ala Trp Thr His Phe His Phe Pro
130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
                180                 185                 190

Tyr Asp Tyr Leu Met Tyr Ala Asp Ile Asp Tyr Asp His Pro Asp Val
                195                 200                 205

Ala Ala Glu Ile Lys Arg Trp Gly Thr Trp Tyr Ala Asn Glu Leu Gln
                210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
                260                 265                 270

Tyr Leu Asn Lys Thr Asn Phe Asn His Ser Val Phe Asp Val Pro Leu
                275                 280                 285

His Tyr Gln Phe His Ala Ala Ser Thr Gln Gly Gly Gly Tyr Asp Met
290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
                340                 345                 350

Thr Arg Glu Ser Gly Tyr Pro Gln Val Phe Tyr Gly Asp Met Tyr Gly
                355                 360                 365

Thr Lys Gly Asp Ser Gln Arg Glu Ile Pro Ala Leu Lys His Lys Ile
370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
                420                 425                 430

Gly Gly Ala Lys Arg Met Tyr Val Gly Arg Gln Asn Ala Gly Glu Thr
                435                 440                 445

Trp His Asp Ile Thr Gly Asn Arg Ser Glu Pro Val Val Ile Asn Ser
450                 455                 460
```

```
Glu Gly Trp Gly Glu Phe His Val Asn Gly Gly Ser Val Ser Ile Tyr
465                 470                 475                 480

Val Gln Arg
```

(2) INFORMATION FOR SEQ ID NO: 4:

(i) SEQUENCE CHARACTERISTICS:
        (A) LENGTH: 511 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 4:

```
Met Lys Gln Gln Lys Arg Leu Tyr Ala Arg Leu Leu Thr Leu Leu Phe
1               5                   10                  15

Ala Leu Ile Phe Leu Pro His Ser Ala Ala Ala Ala Asn Leu
            20                  25                  30

Asn Gly Thr Leu Met Gln Tyr Phe Glu Trp Tyr Met Pro Asn Asp Gly
            35                  40                  45

His Trp Lys Arg Leu Gln Asn Asp Ser Ala Tyr Leu Ala Glu His Gly
        50                  55                  60

Ile Thr Ala Val Trp Ile Pro Pro Ala Tyr Lys Gly Thr Ser Gln Ala
65                  70                  75                  80

Asp Val Gly Tyr Gly Ala Tyr Asp Leu Tyr Asp Leu Gly Glu Phe His
                85                  90                  95

Gln Lys Gly Thr Val Arg Thr Lys Tyr Gly Thr Lys Gly Glu Leu Gln
                100                 105                 110

Ser Ala Ile Lys Ser Leu His Ser Arg Asp Ile Asn Val Tyr Gly Asp
            115                 120                 125

Val Val Ile Asn His Lys Gly Gly Ala Asp Ala Thr Glu Asp Val Thr
        130                 135                 140

Ala Val Glu Val Asp Pro Ala Asp Arg Asn Arg Val Ile Ser Gly Glu
145                 150                 155                 160

His Leu Ile Lys Ala Trp Thr His Phe His Phe Pro Gly Arg Gly Ser
            165                 170                 175

Thr Tyr Ser Asp Phe Lys Trp His Trp Tyr His Phe Asp Gly Thr Asp
            180                 185                 190

Trp Asp Glu Ser Arg Lys Leu Asn Arg Ile Tyr Lys Phe Gln Gly Lys
        195                 200                 205

Ala Trp Asp Trp Glu Val Ser Asn Glu Asn Gly Asn Tyr Asp Tyr Leu
210                 215                 220                 225

Met Tyr Ala Asp Ile Asp Tyr Asp His Pro Asp Val Ala Ala Glu Ile
                230                 235                 240

Lys Arg Trp Gly Thr Trp Tyr Ala Asn Glu Leu Gln Leu Asp Gly Phe
            245                 250                 255

Arg Leu Asp Ala Val Lys His Ile Lys Phe Ser Phe Leu Arg Asp Trp
            260                 265                 270

Val Asn His Val Arg Glu Lys Thr Gly Lys Glu Met Phe Thr Val Ala
        275                 280                 285

Glu Tyr Trp Gln Asn Asp Leu Gly Ala Leu Glu Asn Tyr Leu Asn Lys
290                 295                 300                 305

Thr Asn Phe Asn His Ser Val Phe Asp Val Pro Leu His Tyr Gln Phe
            310                 315                 320
```

```
His Ala Ala Ser Thr Gln Gly Gly Tyr Asp Met Arg Lys Leu Leu
            325                 330                 335

Asn Gly Thr Val Val Ser Lys His Pro Leu Lys Ser Val Thr Phe Val
            340                 345                 350

Asp Asn His Asp Thr Gln Pro Gly Gln Ser Leu Glu Ser Thr Val Gln
            355                 360                 365

Thr Trp Phe Lys Pro Leu Ala Tyr Ala Phe Ile Leu Thr Arg Glu Ser
370                 375                 380                 385

Gly Tyr Pro Gln Val Phe Tyr Gly Asp Met Tyr Gly Thr Lys Gly Asp
                390                 395                 400

Ser Gln Arg Glu Ile Pro Ala Leu Lys His Lys Ile Glu Pro Ile Leu
            405                 410                 415

Lys Ala Arg Lys Gln Tyr Ala Tyr Gly Ala Gln His Asp Tyr Phe Asp
            420                 425                 430

His His Asp Ile Val Gly Trp Thr Arg Glu Gly Asp Ser Ser Val Ala
            435                 440                 445

Asn Ser Gly Leu Ala Ala Leu Ile Thr Asp Gly Pro Gly Gly Ala Lys
450                 455                 460                 465

Arg Met Tyr Val Gly Arg Gln Asn Ala Gly Glu Thr Trp His Asp Ile
                470                 475                 480

Thr Gly Asn Arg Ser Glu Pro Val Val Ile Asn Ser Glu Gly Trp Gly
            485                 490                 495

Glu Phe His Val Asn Gly Gly Ser Val Ser Ile Tyr Val Gln Arg
            500                 505                 510

(2) INFORMATION FOR SEQ ID NO: 5:

(i) SEQUENCE CHARACTERISTICS:
        (A) LENGTH: 520 amino acids
        (B) TYPE: amino acid
        (C) STRANDEDNESS: single
        (D) TOPOLOGY: unknown (ii) MOLECULE TYPE: protein (xi) SEQUENCE DESCRIPTION: SEQ ID NO: 5:

Met Arg Gly Arg Gly Asn Met Ile Gln Lys Arg Lys Arg Thr Val Ser
1               5                   10                  15

Phe Arg Leu Val Leu Met Cys Thr Leu Leu Phe Val Ser Leu Pro Ile
            20                  25                  30

Thr Lys Thr Ser Ala Val Asn Gly Thr Leu Met Gln Tyr Phe Glu Trp
            35                  40                  45

Tyr Thr Pro Asn Asp Gly Gln His Trp Lys Arg Leu Gln Asn Asp Ala
50                  55                  60

Glu His Leu Ser Asp Ile Gly Ile Thr Ala Val Trp Ile Pro Pro Ala
65                  70                  75                  80

Tyr Lys Gly Leu Ser Gln Ser Asp Asn Gly Tyr Gly Pro Tyr Asp Leu
            85                  90                  95

Tyr Asp Leu Gly Glu Phe Gln Gln Lys Gly Thr Val Arg Thr Lys Tyr
            100                 105                 110

Gly Thr Lys Ser Glu Leu Gln Asp Ala Ile Gly Ser Leu His Ser Arg
            115                 120                 125

Asn Val Gln Val Tyr Gly Asp Val Val Leu Asn His Lys Ala Gly Ala
            130                 135                 140

Asp Ala Thr Glu Asp Val Thr Ala Val Glu Val Asn Pro Ala Asn Arg
145                 150                 155                 160
```

```
Asn Gln Glu Thr Ser Glu Glu Tyr Gln Ile Lys Ala Trp Thr Asp Phe
                165                 170                 175

Arg Phe Pro Gly Arg Gly Asn Thr Tyr Ser Asp Phe Lys Trp His Trp
            180                 185                 190

Tyr His Phe Asp Gly Ala Asp Trp Asp Glu Ser Arg Lys Ile Ser Arg
            195                 200                 205

Ile Phe Lys Phe Arg Gly Glu Gly Lys Ala Trp Asp Trp Glu Val Ser
    210                 215                 220

Ser Glu Asn Gly Asn Tyr Asp Tyr Leu Met Tyr Ala Asp Val Asp Tyr
225                 230                 235                 240

Asp His Pro Asp Val Val Ala Glu Thr Lys Lys Trp Gly Ile Trp Tyr
            245                 250                 255

Ala Asn Glu Leu Ser Leu Asp Gly Phe Arg Ile Asp Ala Ala Lys His
            260                 265                 270

Ile Lys Phe Ser Phe Leu Arg Asp Trp Val Gln Ala Val Arg Gln Ala
    275                 280                 285

Thr Gly Lys Glu Met Phe Thr Val Ala Glu Tyr Trp Gln Asn Asn Ala
    290                 295                 300

Gly Lys Leu Glu Asn Tyr Leu Asn Lys Thr Ser Phe Asn Gln Ser Val
305                 310                 315                 320

Phe Asp Val Pro Leu His Phe Asn Leu Gln Ala Ala Ser Ser Gln Gly
            325                 330                 335

Gly Gly Tyr Asp Met Arg Arg Leu Leu Asp Gly Thr Val Val Ser Arg
            340                 345                 350

His Pro Glu Lys Ala Val Thr Phe Val Glu Asn His Asp Thr Gln Pro
            355                 360                 365

Gly Gln Ser Leu Glu Ser Thr Val Gln Thr Trp Phe Lys Pro Leu Ala
            370                 375                 380

Tyr Ala Phe Ile Leu Thr Arg Glu Ser Gly Tyr Pro Gln Val Phe Tyr
385                 390                 395                 400

Gly Asp Met Tyr Gly Thr Lys Gly Thr Ser Pro Lys Glu Ile Pro Ser
            405                 410                 415

Leu Lys Asp Asn Ile Glu Pro Ile Leu Lys Ala Arg Lys Glu Tyr Ala
            420                 425                 430

Tyr Gly Pro Gln His Asp Tyr Ile Asp His Pro Asp Val Ile Gly Trp
            435                 440                 445

Thr Arg Glu Gly Asp Ser Ser Ala Ala Lys Ser Gly Leu Ala Ala Leu
    450                 455                 460

Ile Thr Asp Gly Pro Gly Gly Ser Lys Arg Met Tyr Ala Gly Leu Lys
465                 470                 475                 480

Asn Ala Gly Glu Thr Trp Tyr Asp Ile Thr Gly Asn Arg Ser Asp Thr
            485                 490                 495

Val Lys Ile Gly Ser Asp Gly Trp Gly Glu Phe His Val Asn Asp Gly
            500                 505                 510

Ser Val Ser Ile Tyr Val Gln Lys
            515                 520

(2) INFORMATION FOR SEQ ID NO: 6:

(i) SEQUENCE CHARACTERISTICS:
        (A) LENGTH: 548 amino acids
        (B) TYPE: amino acid
        (C) STRANDEDNESS: single
        (D) TOPOLOGY: unknown (ii) MOLECULE TYPE: protein
```

(xi) SEQUENCE DESCRIPTION: SEQ ID NO: 6:

```
Val Leu Thr Phe His Arg Ile Ile Arg Lys Gly Trp Met Phe Leu Leu
 1               5                  10                  15

Ala Phe Leu Leu Thr Ala Ser Leu Phe Cys Pro Thr Gly Arg His Ala
            20                  25                  30

Lys Ala Ala Pro Phe Asn Gly Thr Met Met Gln Tyr Phe Glu Trp
        35                  40                  45

Tyr Leu Pro Asp Asp Gly Thr Leu Trp Thr Lys Val Ala Asn Glu Ala
    50                  55                  60

Asn Asn Leu Ser Ser Leu Gly Ile Thr Ala Leu Ser Leu Pro Pro Ala
65                  70                  75                  80

Tyr Lys Gly Thr Ser Arg Ser Asp Val Gly Tyr Gly Val Tyr Asp Leu
                85                  90                  95

Tyr Asp Leu Gly Glu Phe Asn Gln Lys Gly Thr Val Arg Thr Lys Tyr
                100                 105                 110

Gly Thr Lys Ala Gln Tyr Leu Gln Ala Ile Gln Ala Ala His Ala Ala
            115                 120                 125

Gly Met Gln Val Tyr Ala Asp Val Val Phe Asp His Lys Gly Gly Ala
    130                 135                 140

Asp Gly Thr Glu Trp Val Asp Ala Val Glu Val Asn Pro Ser Asp Arg
145                 150                 155                 160

Asn Gln Glu Ile Ser Gly Thr Tyr Gln Ile Gln Ala Trp Thr Lys Phe
                165                 170                 175

Asp Phe Pro Gly Arg Gly Asn Thr Tyr Ser Ser Phe Lys Trp Arg Trp
                180                 185                 190

Tyr His Phe Asp Gly Val Asp Trp Asp Glu Ser Arg Lys Leu Ser Arg
            195                 200                 205

Ile Tyr Lys Phe Arg Gly Ile Gly Lys Ala Trp Asp Trp Glu Val Asp
    210                 215                 220

Thr Glu Asn Gly Asn Tyr Asp Tyr Leu Met Tyr Ala Asp Leu Asp Met
225                 230                 235                 240

Asp His Pro Glu Val Val Thr Glu Leu Lys Asn Trp Gly Lys Trp Tyr
                245                 250                 255

Val Asn Thr Thr Asn Ile Asp Gly Phe Arg Leu Asp Gly Leu Lys His
                260                 265                 270

Ile Lys Phe Ser Phe Phe Pro Asp Trp Leu Ser Tyr Val Arg Ser Gln
    275                 280                 285

Thr Gly Lys Pro Leu Phe Thr Val Gly Glu Tyr Trp Ser Tyr Asp Ile
    290                 295                 300

Asn Lys Leu His Asn Tyr Ile Thr Lys Thr Asn Gly Thr Met Ser Leu
305                 310                 315                 320

Phe Asp Ala Pro Leu His Asn Lys Phe Tyr Thr Ala Ser Lys Ser Gly
                325                 330                 335

Gly Ala Phe Asp Met Arg Thr Leu Met Thr Asn Thr Leu Met Lys Asp
            340                 345                 350

Gln Pro Thr Leu Ala Val Thr Phe Val Asp Asn His Asp Thr Asn Pro
    355                 360                 365

Ala Lys Arg Cys Ser His Gly Arg Pro Trp Phe Lys Pro Leu Ala Tyr
        370                 375                 380

Ala Phe Ile Leu Thr Arg Gln Glu Gly Tyr Pro Cys Val Phe Tyr Gly
385                 390                 395                 400

Asp Tyr Tyr Gly Ile Pro Gln Tyr Asn Ile Pro Ser Leu Lys Ser Lys
```

```
                        405                 410                 415
Ile Asp Pro Leu Leu Ile Ala Arg Arg Asp Tyr Ala Tyr Gly Thr Gln
                420                 425                 430

His Asp Tyr Leu Asp His Ser Asp Ile Ile Gly Trp Thr Arg Glu Gly
                435                 440                 445

Val Thr Glu Lys Pro Gly Ser Gly Leu Ala Ala Leu Ile Thr Asp Gly
                450                 455                 460

Ala Gly Arg Ser Lys Trp Met Tyr Val Gly Lys Gln His Ala Gly Lys
465                 470                 475                 480

Val Phe Tyr Asp Leu Thr Gly Asn Arg Ser Asp Thr Val Thr Ile Asn
                    485                 490                 495

Ser Asp Gly Trp Gly Glu Phe Lys Val Asn Gly Gly Ser Val Ser Val
                500                 505                 510

Trp Val Pro Arg Lys Thr Thr Val Ser Thr Ile Ala Arg Pro Ile Thr
                515                 520                 525

Thr Arg Pro Trp Thr Gly Glu Phe Val Arg Trp His Glu Pro Arg Leu
                530                 535                 540

Val Ala Trp Pro
545
```

(2) INFORMATION FOR SEQ ID NO:7:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 7:

```
GATCAAAACA TAAAAAACCG GCCTTGGCCC CGCCGGTTTT TTATTATTTT TGAGCT        56
```

(2) INFORMATION FOR SEQ ID NO: 8:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 8:

```
CAAAAATAAT AAAAAACCGG CGGGGCCAAG GCCGGTTTTT TATGTTTT                  48
```

(2) INFORMATION FOR SEQ ID NO: 9:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 9:

```
CCCATTAAGA TTGGCCGCCT GGGCCGACAT GTTGCTGG                             38
```

(2) INFORMATION FOR SEQ ID NO: 10:

(i) SEQUENCE CHARACTERISTICS:
        (A) LENGTH: 33 base pairs (B) TYPE: nucleic acid
            (C) STRANDEDNESS: single
            (D) TOPOLOGY: linear (xi) SEQUENCE DESCRIPTION: SEQ ID NO: 10:

CCAGCCGACA ATGTCATGGT CGTCGAAATA ATC                                    33

(2) INFORMATION FOR SEQ ID NO: 11:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO: 11:

CCTGATGTCG CAACAGAAAT TAAGAGATGG                                        30

(2) INFORMATION FOR SEQ ID NO: 12:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO: 12:

GTCGCCTTCC CTTGCCCAGC CGACAATGTC                                        30

MUTANT α-AMYLASE COMPRISING MODIFICATION AT RESIDUES CORRESPONDING TO A210, H405 AND/OR T412 IN BACILLUS LICHENIFORMIS

FIELD OF THE INVENTION

The present invention is directed to α-amylases having introduced therein mutations providing additional stability under certain conditions. It is specifically contemplated that the mutant will have altered performance characteristics such as altered stability and/or altered activity profiles.

BACKGROUND OF THE INVENTION

α-Amylases (α-1,4-glucan-4-glucanohydrolase, EC 3.2.1.1) hydrolyze internal α-1,4-glucosidic linkages in starch, largely at random, to produce smaller molecular weight malto-dextrins. α-Amylases are of considerable commercial value, being used in the initial stages (liquefaction) of starch processing; in alcohol production; as cleaning agents in detergent matrices; and in the textile industry for starch desizing α-Amylases are produced by a wide variety of microorganisms including Bacillus and Aspergillus, with most commercial amylases being produced from bacterial sources such as Bacillus licheniformis, Bacillus amyloliquefaciens, Bacillus subtilis, or Bacillus stearothermophilus. In recent years, the preferred enzymes in commercial use have been those from Bacillus licheniformis because of their heat stability and performance under commercial operating conditions.

In general, starch to fructose processing consists of four steps: liquefaction of granular starch, saccharification of the liquefied starch into dextrose, purification, and isomerization to fructose. The object of a starch liquefaction process is to convert a concentrated suspension of starch polymer granules into a solution of soluble shorter chain length dextrins of low viscosity. This step is essential for convenient handling with standard equipment and for efficient conversion to glucose or other sugars. To liquefy granular starch, it is necessary to gelatinize the granules by raising the temperature of the granular starch to over about 72° C. The heating process instantaneously disrupts the insoluble starch granules to produce a water soluble starch solution. The solubilized starch solution is then liquefied by α-amylase (EC 3.2.1.1.).

A common enzymatic liquefaction process involves adjusting the pH of a granular starch slurry to between 6.0 and 6.5, the pH optimum of α-amylase derived from Bacillus licheniformis, with the addition of calcium hydroxide, sodium hydroxide or sodium carbonate. The addition of calcium hydroxide has the advantage of also providing calcium ions which are known to stabilize the α-amylases against inactivation. Upon addition of α-amylases, the suspension is pumped through a steam jet to instantaneously raise the temperature to between 80–115° C. The starch is immediately gelatinized and, due to the presence of α-amylases, depolymerized through random hydrolysis of a (1–4) glycosidic bonds to a fluid mass which is easily pumped.

In a second variation to the liquefaction process, α-amylase is added to the starch suspension, the suspension is held at a temperature of 80–100° C. to partially hydrolyze the starch granules, and the partially hydrolyzed starch suspension is pumped through a jet at temperatures in excess of about 105° C. to thoroughly gelatinize any remaining granular structure. After cooling the gelatinized starch, a second addition of α-amylase can be made to further hydrolyze the starch.

A third variation of this process is called the dry milling process. In dry milling, whole grain is ground and combined with water. The germ is optionally removed by flotation separation or equivalent techniques. The resulting mixture, which contains starch, fiber, protein and other components of the grain, is liquefied using α-amylase. The general practice in the art is to undertake enzymatic liquefaction at a lower temperature when using the dry milling process. Generally, low temperature liquefaction is believed to be less efficient than high temperature liquefaction in converting starch to soluble dextrins.

Typically, after gelatinization the starch solution is held at an elevated temperature in the presence of α-amylase until a DE of 10–20 is achieved, usually a period of 1–3 hours. Dextrose equivalent (DE) is the industry standard for measuring the concentration of total reducing sugars, calculated as D-glucose on a dry weight basis. Unhydrolyzed granular starch has a DE of virtually zero, whereas the DE of D-glucose is defined as 100.

The maximum temperature at which the starch solution containing α-amylase can be held depends upon the microbial source from which the enzyme was obtained and the molecular structure of the α-amylase molecule. α-Amylases produced by wild type strains of Bacillus subtilis or Bacillus amyloliquefaciens are typically used at temperatures no greater than about 90° C. due to excessively rapid thermal inactivation above that temperature, whereas α-amylases produced by wild type strains of Bacillus licheniformis can be used at temperatures up to about 110° C. The presence of starch and calcium ion are known to stabilize α-amylases against inactivation. Nonetheless, α-amylases are used at pH values above 6 to protect against rapid inactivation. At low temperatures, α-amylase from Bacillus licheniformis is known to display hydrolyzing activity on starch substrate at pH values lower than 5. However, when the enzyme is used for starch hydrolysis at common jet temperatures, e.g., between 102° C. and 109° C., the pH must be maintained above at least pH 5.7 to avoid excessively rapid inactivation. The pH requirement unfortunately provides a narrow window of processing opportunity because pH values above 6.0 result in undesirable by-products, e.g., maltulose. Therefore, in reality, liquefaction pH is generally maintained between 5.9 and 6.0 to attain a satisfactory yield of hydrolyzed starch.

Another problem relating to pH of liquefaction is the need to raise the pH of the starch suspension from about 4, the pH of a corn starch suspension as it comes from the wet milling stage, to 5.9–6.0. This pH adjustment requires the costly addition of acid neutralizing chemicals and also requires additional ion-exchange refining of the final starch conversion product to remove the chemical. Moreover, the next process step after liquefaction, typically saccharification of the liquefied starch into glucose with glucoamylase, requires a pH of 4–4.5; therefore, the pH must be adjusted down from 5.9–6.0 to 4–4.5; requiring additional chemical addition and refining steps.

Subsequent to liquefaction, the processed starch is saccharified to glucose with glucoamylase. A problem with present processes occurs when residual starch is present in the saccharification mixture due to an incomplete liquefaction of the starch, e.g., inefficient amylose hydrolysis by amylase. Residual starch is highly resistant to glucoamylase hydrolysis. It represents a yield loss and interferes with downstream filtration of the syrups.

Additionally, many α-amylases are known to require the addition of calcium ion for stability. This further increases the cost of liquefaction.

In U.S. Pat. No. 5,322,778, liquefaction between pH 4.0 and 6.0 was achieved by adding an antioxidant such as bisulfite or a salt thereof, ascorbic acid or a salt thereof, erythorbic acid, or phenolic antioxidants such as butylated hydroxyanisole, butylated hydroxytoluene, or a-tocopherol to the liquefaction slurry. According to this patent, sodium bisulfite must be added in a concentration of greater than 5 mM.

In U.S. Pat. No. 5,180,669, liquefaction between a pH of 5.0 to 6.0 was achieved by the addition of carbonate ion in excess of the amount needed to buffer the solution to the ground starch slurry. Due to an increased pH effect which occurs with addition of carbonate ion, the slurry is generally neutralized by adding a source of hydrogen ion, for example, an inorganic acid such as hydrochloric acid or sulfuric acid.

In PCT Publication No. WO 95/35382, a mutant α-amylase is described having improved oxidation stability and having changes at positions 104, 128, 187 and/or 188 in *B. licheniformis* α-amylase.

In PCT Publication No. WO 96/23873, mutant α-amylases are described which have any of a number of mutations.

In PCT Publication No. WO 94/02597, a mutant α-amylase having improved oxidative stability is described wherein one or more methionines are replaced by any amino acid except cysteine or methionine.

In PCT publication No. WO 94/18314, a mutant α-amylase having improved oxidative stability is described wherein one or more of the methionine, tryptophan, cysteine, histidine or tyrosine residues is replaced with a non-oxidizable amino acid.

In PCT Publication No. WO 91/00353, the performance characteristics and problems associated with liquefaction with wild type *Bacillus licheniformis* α-amylase are approached by genetically engineering the α-amylase to include the specific substitutions Ala-111-Thr, His-133-Tyr and/or Thr-149-Ile.

Studies using recombinant DNA techniques to explore which residues are important for the catalytic activity of amylases and/or to explore the effect of modifying certain amino acids within the active site of various amylases and glycosylases have been conducted by various researchers (Vihinen et al., *J. Biochem.*, Vol. 107, pp. 267–272 (1990); Holm et al., *Protein Engineering*, Vol. 3, pp. 181–191 (1990); Takase et al., *Biochemica et Biophysica Acta*, Vol. 1120, pp. 281–288 (1992); Matsui et al., *FEBS Letters*, Vol. 310, pp. 216–218 (1992); Matsui et al., *Biochemistry*, Vol. 33, pp. 451–458 (1992); Sogaard et al., *J. Biol. Chem.*, Vol. 268, pp. 22480–22484 (1993); Sogaard et al., *Carbohydrate Polymers*, Vol. 21, pp. 137–146 (1993); Svensson, *Plant Mol. Biol.*, Vol. 25, pp. 141–157 (1994); Svensson et al., *J. Biotech.*, Vol. 29, pp. 1–37 (1993)). Researchers have also studied which residues are important for thermal stability (Suzuki et al., *J. Biol. Chem.* Vol. 264, pp. 18933–18938 (1989); Watanabe et al., *Eur. J. Biochem.*, Vol. 226, pp. 277–283 (1994)); and one group has used such methods to introduce mutations at various histidine residues in a *Bacillus licheniformis* amylase, the rationale being that *Bacillus licheniformis* amylase which is known to be relatively thermostable when compared to other similar Bacillus amylases, has an excess of histidines and, therefore, it was suggested that replacing a histidine could affect the thermostability of the enzyme. This work resulted in the identification of stabilizing mutations at the histidine residue at the +133 position and the alanine residue at position +209 (Declerck et al., *J. Biol. Chem.*, Vol. 265, pp. 15481–15488 (1990); FR 2 665 178-A1; Joyet et al., *Bio/Technology*, Vol. 10, pp. 1579–1583 (1992)).

Despite the advances made in the prior art, a need exists for an α-amylase which is more effective in commercial liquefaction processes but allowing activity at lower pH than currently practical. Additionally, a need exists for improved amylases having characteristics which makes them more effective under the conditions of detergent use. Because commercially available amylases are not acceptable under many conditions due to stability problems, for example, the high alkalinity and oxidant (bleach) levels associated with detergents, or temperatures under which they operate, there is a need for an amylase having altered, and preferably increased, performance profiles under such conditions.

SUMMARY OF THE INVENTION

It is an object of the present invention to provide an α-amylase having altered performance profiles.

It is a further object of the present invention to provide an α-amylase having improved stability at high temperature.

Accordingly, the present invention provides an α-amylase having introduced therein a mutation comprising an addition, substitution or deletion at a residue corresponding to A210, H405 and/or T412 in *Bacillus licheniformis* α-amylase. In a particularly preferred embodiment of the invention, the α-amylase is derived from a bacterial or a fungal source and comprises a substitution corresponding to *Bacillus licheniformis*. Most preferably, the α-amylase is derived from Bacillus and the mutations correspond to A210T, H405D and/or T412A in *Bacillus licheniformis*.

The invention further comprises nucleic acids encoding such mutant amylases, vectors comprising such nucleic acids, host cells transformed with such vectors and methods of expressing mutant α-amylases utilizing such host cells.

The invention further comprises the use of the mutant α-amylases according to the invention to liquefy starch in the starch processing pathway to glucose or other starch derivatives, as an additive in detergents such as laundry and dishwashing detergents, as a baking aid and for desizing of textiles.

BRIEF DESCRIPTION OF THE DRAWINGS

FIGS. 1A–1C illustrate the DNA sequence of the gene for α-amylase from *Bacillus licheniformis* (NCIB 8061) (SEQ ID NO:1) and deduced amino acid sequence of the translation product (SEQ ID NO:2) as described by Gray et al., *J. Bacteriology*, Vol. 166, pp. 635–643 (1986).

FIG. 2 illustrates the amino acid sequence (SEQ ID NO:3) of the mature α-amylase enzyme from *Bacillus licheniformis*.

FIGS. 3A and 3B illustrate an alignment of the primary structures of three Bacillus α-amylases. The *Bacillus licheniformis* α-amylase (Am-Lich) (SEQ ID NO:4) is described by Gray et al., *J. Bacteriology*, Vol.166, pp. 635–643 (1986); the *Bacillus amyloliquefaciens* α-amylase (Am-Amylo) (SEQ ID NO:5) is described by Takkinen et al., *J. Biol. Chem.*, Vol. 258, pp.1007–1013 (1983); and the *Bacillus stearothermophilus* α-amylase (Am-Stearo) (SEQ ID NO:6) is described by Ihara et al., *J. Biochem.*, Vol. 98, pp. 95–103 (1985).

FIG. 4 illustrates plasmid pHP13 wherein $Cm^R$ refers to chloramphenicol resistance, $Em^R$ refers to erythromycin resistance and Rep pTA1060 refers to the origin of replication from plasmid pTA1060.

FIG. 5 illustrates the pBLapr plasmid wherein BL AA refers to *Bacillus licheniformis* α-amylase gene; aprE refers to the promoter and signal peptide encoding region of the aprE gene; AmpR refers to the ampicillin resistant gene from pBR322; and CAT refers to the chloramphenicol resistance gene from pC194.

DETAILED DESCRIPTION

Figure 6:
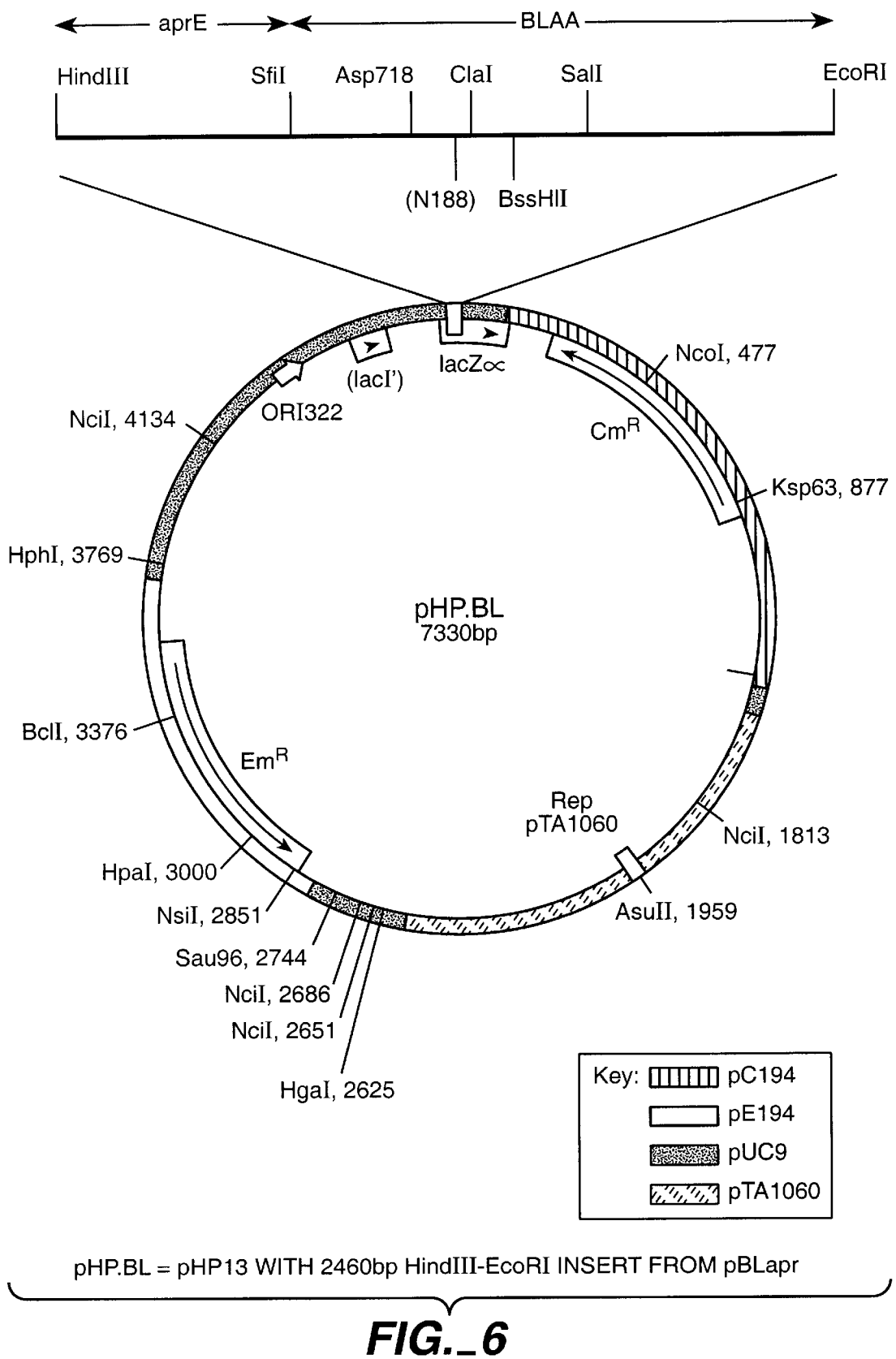
FIG. 6 illustrates the pHP.BL plasmid carrying the gene for *Bacillus licheniformis* α-amylase.

"α-Amylase" means an enzymatic activity which cleaves or hydrolyzes the α(1–4)glycosidic bond, e.g., that in starch, amylopectin or amylose polymers. α-Amylase as used herein includes naturally occurring α-amylases as well as recombinant α-amylases. Preferred α-amylases in the present invention are those derived from *Bacillus licheniformis, Bacillus amyloliquefaciens* or *Bacillus stearothermophilus,* as well as fungal (α-amylases such as those derived from Aspergillus (i.e., *A. oryzae* and *A. niger*).

"Recombinant α-amylase" means an α-amylase in which the DNA sequence encoding the naturally occurring α-amylase is modified to produce a mutant DNA sequence which encodes the substitution, insertion or deletion of one or more amino acids in the α-amylase sequence compared to the naturally occurring α-amylase.

"Expression vector" means a DNA construct comprising a DNA sequence which is operably linked to a suitable control sequence capable of effecting the expression of said DNA in a suitable host. Such control sequences may include a promoter to effect transcription, an optional operator sequence to control such transcription, a sequence encoding suitable mRNA ribosome-binding sites, and sequences which control termination of transcription and translation. A preferred promoter is the *Bacillus subtilis* aprE promoter. The vector may be a plasmid, a phage particle, or simply a potential genomic insert. Once transformed into a suitable host, the vector may replicate and function independently of the host genome, or may, in some instances, integrate into the genome itself. In the present specification, plasmid and vector are sometimes used interchangeably as the plasmid is the most commonly used form of vector at present. However, the invention is intended to include such other forms of expression vectors which serve equivalent functions and which are, or become, known in the art.

"Host strain" or "host cell" means a suitable host for an expression vector comprising DNA encoding the α-amylase according to the present invention. Host cells useful in the present invention are generally procaryotic or eucaryotic hosts, including any transformable microorganism in which the expression of α-amylase according to the present invention can be achieved. Specifically, host strains of the same species or genus from which the α-amylase is derived are suitable, such as a Bacillus strain. Preferably, an α-amylase negative Bacillus strain (genes deleted) and/or an α-amylase and protease deleted Bacillus strain (ΔamyE, Δapr, Δnpr) is used. Host cells are transformed or transfected with vectors constructed using recombinant DNA techniques. Such transformed host cells are capable of either replicating vectors encoding the α-amylase and its variants (mutants) or expressing the desired α-amylase.

"Liquefaction" or "liquefy" means a process by which starch is converted to shorter chain and less viscous dextrins. Generally, this process involves gelatinization of starch simultaneously with or followed by the addition of α-amylase.

According to the present invention, a mutant α-amylase is provided that has introduced therein a substitution, addition or deletion at A210, H405 and/or T412. Deletion, addition or substitution of an amino acid as used herein refers to any modification of the amino acid sequence of the precursor α-amylase itself, but preferably refers to using genetic engineering to mutate a nucleic acid encoding the precursor α-amylase so as to encode the deleted, substituted or added residue in the expressed protein. The precursor α-amylases include naturally occurring α-amylases and recombinant α-amylases. Modification of the precursor DNA sequence which encodes the amino acid sequence of the precursor α-amylase can be by methods described herein and in commonly owned U.S. Pat. Nos. 4,760,025 and 5,185,258, incorporated herein by reference.

Also provided is a nucleic acid molecule (DNA) which encodes an amino acid sequence comprising the mutant α-amylase provided by the present invention, expression systems incorporating such DNA including vectors and phages, host cells transformed with such DNA, and antisense strands of DNA corresponding to the DNA molecule which encodes the amino acid sequence. Similarly, the present invention includes a method for producing a mutant (α-amylase by expressing the DNA incorporated in an expression system which has been transformed into a host cell. The mutant α-amylase of the invention may be used in liquefaction of starch, as an ingredient in laundry detergents, automatic dishwashing detergents, hard surface cleaning products, in food processing including baking applications, in textile processing including as a desize agent, or in any other application in which α-amylase activity is useful.

The precursor α-amylase is produced by any source capable of producing α-amylase. Suitable sources of α-amylases are prokaryotic or eukaryotic organisms, including fungi, bacteria, plants or animals. Preferably, the precursor α-amylase is produced by a Bacillus; more preferably, by *Bacillus licheniformis, Bacillus amyloliquefaciens* or *Bacillus stearothermophilus;* most preferably, the precursor α-amylase is derived from *Bacillus licheniformis*.

Homologies have been found between almost all endo-amylases sequenced to date, ranging from plants, mammals, and bacteria (Nakajima et al., *Appl. Microbiol. Biotechnol.,* Vol. 23, pp. 355–360 (1986); Rogers, *Biochem. Biophys. Res. Commun.,* Vol. 128, pp. 470–476 (1985); Janecek, *Eur. J. Biochem.,* Vol. 224, pp. 519–524 (1994)). There are four areas of particularly high homology in certain Bacillus amylases, as shown in FIG. 3, wherein the underlined sections designate the areas of high homology. Sequence alignments have also been used to map the relationship between Bacillus endo-amylases (Feng et al., *J. Molec. Evol.,* Vol. 35, pp. 351–360 (1987)). The relative sequence homology between *Bacillus stearothermophilus* and *Bacillus licheniformis* amylase is about 66% and that between *Bacillus licheniformis* and *Bacillus amyloliquefaciens* amylases is about 81%, as determined by Holm et al., *Protein Engineering,* Vol. 3, No. 3, pp. 181–191 (1990). While sequence homology is important, it is generally recognized that structural homology is also important in comparing amylases or other enzymes. For example, structural homology between fungal amylases and bacterial amylase has been suggested and, therefore, fungal amylases are encompassed within the present invention.

Among others, addition, deletion or substitution at residues corresponding to A210, H405 and/or T412 in *Bacillus licheniformis* α-amylase are identified herein. Thus, specific residues such as A210 refer to an amino acid position number (i.e., +210) which references the number assigned to the mature *Bacillus licheniformis* α-amylase sequence illustrated in FIG. 1. The invention, however, is not limited to the mutation of the particular mature α-amylase of *Bacillus*

*licheniformis* but extends to precursor α-amylases containing amino acid residues at positions which are equivalent to the particular identified residue in *Bacillus licheniformis* α-amylase. A residue of a precursor α-amylase is equivalent to a residue of *Bacillus licheniformis* α-amylase if it is either homologous (i.e., corresponds in position for either the primary or tertiary structure) or analogous to a specific residue or portion of that residue in *Bacillus licheniformis* α-amylase (i.e., having the same or similar functional capacity to combine, react, or interact chemically or structurally).

In order to establish homology to primary structure, the amino acid sequence of a precursor α-amylase is directly compared to the *Bacillus licheniformis* α-amylase primary sequence and particularly to a set of residues known to be invariant to all α-amylases for which sequences are known (see e.g., FIG. 3). It is possible also to determine equivalent residues by tertiary structure analysis of the crystal structures reported for porcine pancreatic α-amylase (Buisson et al., *EMBO Journal*, Vol. 6, pp. 3909–3916 (1987); Qian et al., *Biochemistry, Vol.* 33, pp. 6284–6294 (1994); Larson et al., *J. Mol. Biol.*, Vol. 235, pp. 1560–1584 (1994)); Taka-amylase A from *Aspergillus oryzae* (Matsuura et al., *J. Biochem.* (Tokyo), Vol. 95, pp. 697–702 (1984)); and an acid α-amylase from *A. niger* (Boel et al.. *Biochemistry*, Vol. 29, pp. 6244–6249 (1990)), with the former two structures being similar, and for barley α-amylase (Vallee et al.,*J. Mol. Biol.*, Vol. 236, pp. 368–371(1994); Kadziola, *J. Mol. Biol.*, Vol. 239, pp.104–121 (1994)). Several preliminary studies have been published related to the secondary structure of α-amylase, i.e., (Suzuki et al., *J. Biochem.*, Vol. 108, pp. 379–381 (1990); Lee et al., *Arch. Biochem. Biophys*, Vol. 291, pp. 255–257 (1991); Chang et al., *J. Mol. Biol.*, Vol. 229, pp. 235–238 (1993); Mizuno et al., *J. Mol. Biol.*, Vol. 234, pp. 1282–1283 (1993)), and at least one structure has been published for crystalline *Bacillus licheniformis* α-amylase (Machius et al., *J. Mol. Biol.* Vol. 246, pp. 545–549 (1995)). However, several researchers have predicted common super-secondary structures between glucanases (MacGregor et al., *Biochem. J.*, Vol. 259, pp. 145–152 (1989)) and within α-amylases and other starch-metabolising enzymes (Jaspersen, *J. Prot. Chem.* Vol. 12, pp. 791–805 (1993); MacGregor, *Starke*, Vol. 45, pp. 232–237 (1993)); and sequence similarities between enzymes with similar super-secondary structures to α-amylases (Janecek, *FEBS Letters*, Vol. 316, pp. 23–26 (1993); Janecek et al.,*J. Prot. Chem.*, Vol. 12, pp. 509–514 (1993)). A structure for the *Bacillus stearothermophilus* enzyme has been modeled on that of Taka-amylase A (Holm et al.,*Protein Engineering*, Vol. 3, pp. 181–191 (1990)). The four highly conserved regions shown in FIG. 3 contain many residues thought to be part of the active-site (Matsuura et al., *J. Biochem.* (Tokyo), Vol. 95, pp. 697–702 (1984); Buisson et al., *EMBO Journal*, Vol. 6, pp. 3909–3916 (1987); Vihinen et al., *J. Biochem.*, Vol. 107, pp. 267–272 (1990)) including His +105; Arg +229; Asp +231; His +235; Glu +261 and Asp +328 under the *Bacillus licheniformis* numbering system.

α-Amylases according to the present invention which exhibit altered performance characteristics providing desirable and unexpected results are useful in the various applications for which α-amylases are commonly used. For example, α-amylases according to the present invention which exhibit altered performance characteristics at low pH, including improved thermostability, improved pH stability and/or improved oxidative stability, are useful in low pH liquefaction of starch. Enhanced thermostability will be useful in extending the shelf life of products which incorporate them. Enhanced oxidative stability or improved performance is particularly desirable in cleaning products, and for extending the shelf life of α-amylase in the presence of bleach, perborate, percarbonate or peracids used in such cleaning products. To the contrary, reduced thermal stability or oxidative stability may be useful in industrial processes which require the rapid and efficient quenching of amylolytic activity.

α-Amylases of the present invention which exhibit improved low pH stability will be especially useful in starch processing and particularly in starch liquefaction. Conditions present during commercially desirable liquefaction processes characteristically include low pH, high temperature and potential oxidation conditions requiring α-amylases exhibiting improved low pH performance, improved thermal stability and improved oxidative stability. Accordingly, α-amylases according to the present invention which are particularly useful in liquefaction exhibit improved performance at a pH of less than about 6, preferably less than about 5.5, and most preferably less than about 5.0. Additionally, α-amylases according to the present invention which exhibit increased thermal stability at temperatures of between about 80–120° C., and preferably between about 100–110° C., and increased stability in the presence of oxidants will be particularly useful.

Additional components known by those skilled in the art to be useful in liquefaction, including, for example, antioxidants, calcium, ions, salts or other enzymes such as endoglycosidases, cellulases, proteases, lipases or other amylase enzymes may be added depending on the intended reaction conditions. For example, combinations of the α-amylase according to the present invention with α-amylases from other sources may provide unique action profiles which find particular use under specific liquefaction conditions. In particular, it is contemplated that the combination of the α-amylase according to the present invention with α-amylase derived from *Bacillus stearothermophilus* will provide enhanced liquefaction at pH values below 5.5 due to complementary action patterns.

During liquefaction, starch, specifically granular starch slurries from either a wet or dry milled process, is treated with an α-amylase of the present invention according to known liquefaction techniques. Generally, in the first step of the starch degradation process, the starch slurry is gelatinized by heating at a relatively high temperature (between about 80° C. and about 110° C.). After the starch slurry is gelatinized, it is liquefied using an α-amylase.

In another embodiment of the present invention, detergent compositions in either liquid, gel or granular form, which comprise the α-amylase according to the present invention may be useful. Such detergent compositions will particularly benefit from the addition of an α-amylase according to the present invention which has increased thermal stability to improve shelf-life or increased oxidative stability such that the α-amylase has improved resistance to bleach or peracid compounds commonly present in detergents. Thus, α-amylase according to the present invention may be advantageously formulated into known powdered, liquid or gel detergents having a pH of between about 6.5 and about 12.0. Detergent compositions comprising the α-amylase according to the present invention may further include other enzymes such as endoglycosidases, cellulases, proteases, lipases or other amylase enzymes, particularly α-amylase derived from *Bacillus stearothermophilus*, as well as additional ingredients as generally known in the art.

A preferred embodiment of the present invention further comprises, in addition to the substitution, addition or deletion of residues as provided herein, any one or more of the substitutions known in the art to confer stability or increased activity. For example, the deletion or substitution of a methionine residue or a tryptophan residue, for example M15, M197 or W138 as described in WO 94/18314, the disclosure of which is incorporated by reference; substitution at H133Y as described in PCT Publication No. WO 91/00353; or substitution at A209 as described in DeClerck, et al., *J. Biol. Chem.*, Vol. 265, pp. 15481–15488 (1990); or any of the substitutions described in PCT Publication Nos. WO 95/10603, WO 96/23873 and WO 96/23874. In particularly preferred embodiments, the α-amylase according to the present invention may further comprise a deletion or substitution at one or more residues corresponding to M15, A33, A52, S85, N96, V129, H133, S148, S187, N188, A209, A269 and/or A379 in *Bacillus licheniformis*.

Embodiments of the present invention which comprise a combination of the α-amylase according to the present invention with protease enzymes preferably include oxidatively stable proteases such as those described in U.S. Re. 34,606, incorporated herein by reference, as well as commercially available enzymes such as DURAZYM (Novo Nordisk) and PURAFECT® OxP (Genencor International, Inc.). Methods for making such protease mutants (oxidatively stable proteases), and particularly such mutants having a substitution for the methionine at a position equivalent to M222 in *Bacillus amyloliquefaciens*, are described in U.S. Re. 34,606.

An additional embodiment of the present invention comprises DNA encoding an α-amylase according to the present invention and expression vectors comprising such DNA. The DNA sequences may be expressed by operably linking them to an expression control sequence in an appropriate expression vector and employing that expression vector to transform an appropriate host according to well known techniques. A wide variety of host/expression vector combinations may be employed in expressing the DNA sequences of this invention. Useful expression vectors, for example, include segments of chromosomal, non-chromosomal and synthetic DNA sequences, such as the various known plasmids and phages useful for this purpose. In addition, any of a wide variety of expression control sequences are generally used in these vectors. For example, Applicants have discovered that a preferred expression control sequence for Bacillus transformants is the aprE signal peptide derived from *Bacillus subtilis*.

A wide variety of host cells are also useful in expressing the DNA sequences of this invention. These hosts may include well known eukaryotic and prokaryotic hosts, such as strains of *E. coli*, Pseudomonas, Bacillus, Streptomyces, various fungi, yeast and animal cells. Preferably, the host expresses the α-amylase of the present invention extracellularly to facilitate purification and downstream processing. Expression and purification of the mutant α-amylase of the invention may be effected through art-recognized means for carrying out such processes.

The improved α-amylases according to the present invention are contemplated to provide important advantages when compared to wild type Bacillus α-amylases. For example, one advantage is the increased activity found at low pH and high temperatures typical of common starch liquefaction methods. Other advantages may include increased high pH and oxidative stability which facilitates their use in detergents; more complete hydrolysis of starch molecules is achieved which reduces residual starch in the processing stream; improved stability in the absence of calcium ion; and that the addition of equal protein doses of α-amylase according to the invention may provide superior performance when compared to wild type *Bacillus licheniformis* α-amylase due to improvements in both specific activity and stability under stressed conditions.

The following is presented by way of example and is not to be construed as a limitation to the scope of the claims. Abbreviations used herein, particularly three letter or one letter notations for amino acids are described in Dale, J. W., *Molecular Genetics of Bacteria*, John Wiley & Sons, (1989) Appendix B.

EXAMPLES

Example 1

Construction of Plasmid pHP.BL

The α-amylase gene shown in FIG. 1 was cloned from *Bacillus licheniformis* NCIB8061 (Gray et al., *J. Bacteriology*, Vol. 166, pp. 635–643 (1986)). The 1.72 kb PstI-SstI fragment, encoding the last three residues of the signal sequence, the entire mature protein and the terminator region, was subcloned into M13mp18. A synthetic terminator was added between the BclI and SstI sites using a synthetic oligonucleotide cassette of the form:

5'-GATCAAAACATCAAAAAACCGGCCTTG-
    GCCCCGCCGGTTTTTTATTATTTTTGAGGCT (SEQ ID NO:7)

3'-TTTTGTATTTTTTGGCCGGAAC-
    CGGGGCGGCCAAAAAATAATAAAAAC-5' (SEQ ID NO:8)

designed to contain the *Bacillus amyloliquefaciens* subtilisin transcriptional terminator (Wells et al., *Nucleic Acid Research*, Vol. 11, pp. 7911–7925 (1983)).

The pBLapr plasmid was constructed carrying the gene for the *Bacillus licheniformis* α-amylase. As illustrated in FIG. 5, pBLapr comprises a 6.1 kb plasmid including the ampicillin resistance gene from pBR322 and the chloramphenicol resistance gene from pC194, the aprE promoter and the gene encoding for the *Bacillus licheniformis* α-amylase ("BL AA"). The aprE promoter was constructed from a 660 bp HindIII-PstI fragment encoding for the promoter and signal sequence of the *Bacillus subtilis* alkaline protease. The PstI site was removed, and an SfiI site added close to the aprE/BL AA junction. The BL AA gene comprises the 1720 bp PstI-SstI fragment described above. In the work described herein, pBLapr was constructed with an SfiI site adjacent to the 5' end of the start of the coding sequence for the mature amylase gene. Specifically, the 5' end of the pBLapr construction was subcloned on an EcoRI-SstII fragment from pBLapr into M13BM20 (Boehringer Mannheim) to obtain a coding-strand template for the mutagenic oligonucleotide below:

5'-CCC ATT AAG ATT <u>GGC CGC CTG GGC C</u>GA CAT GTT
    GCT GG-3'    (SEQ ID NO:9)

This primer introduced an SfiI site (indicated by underlining) which allowed correct forms to be screened for by the presence of this unique restriction site. Subcloning the EcoRI-SstII fragment back into the pBLapr vector gave a version of the plasmid containing an SfiI site.

Plasmid pHP13 (Haima et al., *Mol. Gen. Genet.*, Vol. 209, pp. 335–342 (1987)) (FIG. 4) was digested with restriction enzymes EcoRI and HindIII and the resulting vector purified on a polyacrymide gel and then eluted. Plasmid pBLapr was digested with HindIII, Asp718 and in a separate incubation with Asp718, EcoRI and gel purified. Two bands, HindIII-Asp718 (1203 bp) and Asp718-EcoRI (1253 bp) were gel purified, eluted from the gel and ligated into the vector by a 3-way ligation, to give plasmid pHP.BL, the plasmid used in expression of the α-amylase (FIG. 6).

Example 2

Construction of Plasmid Encoding α-Amylase Comprising A210T/H405A/T412D

A pBLapr plasmid having threonine substituted for methionine at amino acid 15 was constructed according to U.S. patent application Ser. No. 08/194,664 (PCT Publication No. WO 94/18314). To introduce the mutations, the following mutagenic primers encoding for substitutions of A210T/M405D/T412A are used together with non-mutagenic primers to introduce the desired mutations into linear multiple tandem repeats of the plasmid by the method of multimerization as described below.

H405D (L)

(411) CCA GCC GAC AAT GTC ATG GTC GTC GAA ATA ATC
(401)                                                    (SEQ ID NO:10)

A210T (R)

(206) CCT GAT GTC GCA ACA GAA ATT AAG AGA TGG
(215)                                                    (SEQ ID NO:11)

T412A (L)

(416) GTC GCC TTC CCT TGC CCA GCC GAC AAT GTC
(407)                                                    (SEQ ID NO:12)

A fragment starting at the appropriate mutagenic primer for the desired mutation (shown above) and ending at the end of the non-mutagenic primer is generated by PCR. This fragment is gel purified and used to generate long, linear tandem repeats of the plasmid encoding the desired mutations as follows:

The vector (pBLapr) is linearized by restriction digest (Sal I) and purified using Qiagen kits. The multimerization reactions typically contain 5.4 mM Tris buffer pH 8.0, 1x XL buffer (Perkin Elmer, Branchburg, N.J.), 0.2 mM dNTPs, 1.1 mM Mg(OAC)$_2$, 3 ng/μl incoming fragment, 0.15 ng/μl linearized vector, 4 U rTth DNA polymerase, XL (Perkin Elmer) in 100 μl reaction mixture. PCR reactions are typically performed in a thermocycler under the following conditions: 20 cycles (15s 94° C., 5 min 68° C.) and 15 cycles (15s 94° C., 10 min 68° C.).

The resulting multimers are transformed directly into *B. subtilis* competent cells using standard techniques. Plasmid DNA is isolated from the transformants using standard techniques.

Mutations were confirmed by dideoxy sequencing (Sanger et al., *Proc. Natl. Acad. Sci. U.S.A.*, Vol. 74, pp. 5463–5467 (1977)).

Example 3

Transformation of Plasmids Into *Bacillus subtilis*, Expression and Purification of Mutant α-Amylase α-Amylase may be expressed in *Bacillus subtilis* after transformation with the plasmids described above. pHP13 is a plasmid able to replicate in *E. coli* and in *Bacillus subtilis*. Plasmids containing different variants were constructed using *E. coli* strain MM294, the plasmids isolated and then transformed into *Bacillus subtilis* as described in Anagnostopoulos et al., *J. Bacter.*, Vol. 81, pp. 741–746 (1961). The Bacillus strain had been deleted for two proteases (Δapr, Δnpr) (see e.g., Ferrari et al., U.S. Pat. No. 5,264,366) and for amylase (ΔamyE) (see e.g., Stahl et al., *J. Bacter.*, Vol. 158, pp. 411–418 (1984)). After transformation, the sacU (Hy) mutation (Henner et al., *J. Bacter.*, Vol., 170, pp. 296–300 (1988)) was introduced by PBS-1 mediated transduction (Hoch, *J. Bact.*, Vol. 154, pp. 1513–1515 (1983)).

Secreted amylase was recovered from *Bacillus subtilis* cultures as follows: Sodium chloride was added to the culture supernatant to 20 mM and the pH was adjusted to approximately 7.0 with 1 M tris buffer, pH 7.2. The supernatant was then heated to 70° C. for 15 minutes, and the precipitate removed by centrifugation. Ammonium sulphate was added the supernatant to 1.3M followed by 20 ml phenyl sepharose fast flow 6 (high substitution) resin (Pharmacia). Following agitation, resin was separated by filtration, and washed in 1M ammonium sulphate, 20 mM ammonium acetate pH 7.0, 5 mM calcium chloride. The bound amylase was eluted into 20 mM ammonium acetate pH 7.0, 5 mM calcium chloride, and precipated by addition of ammonium sulphate to 70% saturation. The precipated material was pelleted by centrifugation, redissolved in a minimum volume of 20 mM ammonium acetate pH 7.0, 5 mM calcium chloride and dialysed against the same buffer.

Concentration was determined using the soluble substrate assay, assuming wild-type specific activity.

Example 4

Assay for Determining α-Amylase Activity

Soluble Substrate Assay: A rate assay was developed based on an end-point assay kit supplied by Megazyme (Aust.) Pty. Ltd. A vial of substrate (p-nitrophenyl maltoheptaoside, BPNPG7) was dissolved in 10 ml of sterile water followed by a 1:4 dilution in assay buffer (50 mM maleate buffer, pH 6.7, 5 mM calcium chloride, 0.002% Tween20). Assays were performed by adding 10 μl of amylase to 790 μl of the substrate in a cuvette at 25° C. Rates of hydrolysis were measured as the rate of change of absorbance at 410 nm, after a delay of 75 seconds. The assay was linear up to rates of 0.2 absorption units/min.

α-Amylase protein concentration was measured using the standard Bio-Rad Assay (Bio-Rad Laboratories) based on the method of Bradford, *Anal. Biochem.*, Vol. 72, p. 248 (1976) using bovine serum albumin standards.

Example 5

Preparation and Testing of Additional Mutant Alpha-Amylases for Thermal Stability Mutant *B. licheniformis* alpha-amylase was prepared having substitutions at A210T/H405D/T412A. Thermal inactivation rate for the mutant was measured according to the following procedure. Amylase stock solutions were dialysed extensively into 20 mM ammonium acetate, 4 mM CaCl$_2$ pH 6.5. Each sample was stored at 4° C. For measurement of stability, this stock was diluted >50 fold into 50 mM ammonium acetate, 5 mM CaCl$_2$, 0.02% Tween 20 pH 4.8 to a final concentration of between 30 and 50 μg/ml. Six 100 μl aliquots were put into eppendorf tubes and placed into a water bath or hot block at 83° C. The eppendorf tubes were removed at regular, measured intervals of between 30 seconds and 5 minutes and placed on ice to stop the inactivation. The residual activity was assayed using a soluble substrate as described in Example 4. The natural log of the activity was plotted against time of incubation, and the rate constant for inactivation obtained from the slope of the straight line. Results are provided in Table 1.

TABLE 1

| Amylase | Relative Half-Life | |
|---|---|---|
| | Exp. #1 | Exp. #2 |
| wild type | 1.00 | 1.00 |
| wild type | 1.01 | XX |
| A210T/H405D/ | 1.06 | 1.05 |
| T412A | | |

As shown in Table 1, mutant enzymes having introduced therein the mutations according to the invention have significantly improved stability under the conditions of the assay.

We claim:

1. A mutant α-amylase which is derived from a precursor α-amylase by the substitution to said precursor α-amylase of a residue corresponding to T412 in *Bacillus licheniformis* α-amylase as numbered in SEQ. ID NO:3.

2. The α-amylase according to claim 1, wherein said α-amylase comprises a substitution pattern corresponding to the group consisting of A210T/T412A, H405D/T412A and A210T/H405D/T412A in *Bacillus licheniformis* α-amylase.

3. The α-amylase according to claim 1, wherein said α-amylase is derived from a bacterial or fungal source.

4. The α-amylase according to claim 1, wherein said α-amylase is derived from Bacillus.

5. The α-amylase according to claim 4, wherein said α-amylase is derived from *Bacillus licheniformis, Bacillus stearothermophilus* or *Bacillus amyloliquefaciens*.

6. The α-amylase according to claim 1 wherein said α-amylase further comprises the substitution of a residue corresponding to M15, A33, A52, S85, N96, V129, H133, S148N, S187, N188, A209, A269 and/or A379 in *Bacillus licheniformis* α-amylase as numbered in SEQ. ID NO:3.

7. The α-amylase according to claim 1, wherein substitution further comprises deleting a residue corresponding to M15T, W138Y and/or M197T in *Bacillus licheniformis* as numbered in SEQ. ID NO:3.

8. An α-amylase according to claims 1, 2 or 6 having enhanced low pH performance and/or increased thermostability.

9. A detergent composition comprising the α-amylase according to claim 1.

10. The detergent composition according to claim 9, wherein said detergent is useful for cleaning soiled laundry and/or soiled dishes.

11. A method of liquefying starch comprising contacting a slurry of starch with the α-amylase according to claim 1.

* * * * *